US009389209B2

(12) United States Patent
Ergang et al.

(10) Patent No.: US 9,389,209 B2

(45) Date of Patent: Jul. 12, 2016

(54) OXOANION CONCENTRATION DETERMINATION USING ALUMINUM REAGENTS

(71) Applicant: Ecolab USA Inc., Saint Paul, MN (US)

(72) Inventors: Nicholas S. Ergang, Glen Ellyn, IL (US); Ronald V. Davis, Geneva, IL (US)

(73) Assignee: ECOLAB USA INC., St. Paul, MN (US)

(*) Notice: Subject to any disclaimer, the term of this patent is extended or adjusted under 35 U.S.C. 154(b) by 0 days.

(21) Appl. No.: 14/478,962

(22) Filed: Sep. 5, 2014

(65) Prior Publication Data

US 2016/0069849 A1 Mar. 10, 2016

(51) Int. Cl.

| | |
|---|---|
| ***C02F 1/66*** | (2006.01) |
| ***C02F 1/52*** | (2006.01) |
| ***G01N 31/22*** | (2006.01) |

(52) U.S. Cl.

CPC .............. *G01N 31/22* (2013.01); *C02F 1/5236* (2013.01); *C02F 1/66* (2013.01); *Y10T 436/18* (2015.01)

(58) Field of Classification Search

CPC .......... C02F 1/5236; C02F 1/008; C02F 1/66; C02F 1/52; C02F 1/00; Y10T 436/00; Y10T 436/18

USPC .......... 436/127, 119, 172; 210/638, 709, 724, 210/634, 702, 723, 600

See application file for complete search history.

(56) References Cited

U.S. PATENT DOCUMENTS

| | | | | |
|---|---|---|---|---|
| 4,059,513 | A | 11/1977 | Zadera | |
| 4,906,408 | A | 3/1990 | Bouniol | |
| 4,935,146 | A | 6/1990 | O'Neill et al. | |
| 5,372,717 | A | 12/1994 | Abolt et al. | |
| 5,443,730 | A | 8/1995 | Letourneux et al. | |
| 5,547,588 | A | 8/1996 | Hassett | |
| 5,587,079 | A | 12/1996 | Rowley et al. | |
| 5,695,646 | A | 12/1997 | Graef | |
| 6,210,589 | B1 | 4/2001 | Lee et al. | |
| 6,280,630 | B1 | 8/2001 | Ramsay | |
| 6,280,635 | B1 | 8/2001 | Moriarty et al. | |
| 6,312,644 | B1 | 11/2001 | Moriarty et al. | |
| 6,358,746 | B1 | 3/2002 | Moriarty et al. | |
| 6,369,894 | B1 | 4/2002 | Rasimas et al. | |
| 6,645,428 | B1 | 11/2003 | Morris et al. | |
| 6,811,704 | B2 | 11/2004 | Cho et al. | |
| 7,144,362 | B2 | 12/2006 | Roper, Jr. | |
| 7,179,384 | B2 | 2/2007 | Moriarty et al. | |
| 7,601,789 | B2 | 10/2009 | Morris et al. | |
| 7,772,009 | B2 * | 8/2010 | Davis et al. | 436/172 |
| 7,875,720 | B2 | 1/2011 | Morris et al. | |
| 7,914,676 | B2 | 3/2011 | Riebensahm | |
| 2007/0259441 | A1 | 11/2007 | Saaski | |
| 2011/0132839 | A1 | 6/2011 | Zuback et al. | |
| 2011/0163032 | A1 | 7/2011 | Alexander et al. | |
| 2012/0031850 | A1 | 2/2012 | Smith et al. | |
| 2012/0160770 | A1 | 6/2012 | Banerjee et al. | |
| 2012/0193296 | A1 | 8/2012 | Bhaduri et al. | |
| 2012/0315659 | A1 | 12/2012 | Andreescu et al. | |
| 2014/0251906 | A1 | 9/2014 | Ergang et al. | |
| 2015/0083669 | A1 | 3/2015 | Matherly et al. | |

FOREIGN PATENT DOCUMENTS

| | | | |
|---|---|---|---|
| DE | 4005469 | A1 | 8/1991 |
| EP | 0250626 | A1 | 1/1988 |
| EP | 0584502 | A2 | 3/1994 |
| EP | 0623559 | A1 | 11/1994 |
| GB | 2449996 | | 6/2007 |
| JP | 2001-356395 | A | 12/2001 |
| JP | 2003-154273 | A | 5/2003 |
| JP | 2003-154372 | | 5/2003 |
| WO | 2014/033361 | A1 | 3/2014 |

OTHER PUBLICATIONS

McAuley, B., Quantitative detection of aqueous arsenic and other oxoanions using attenuated total reflectance infrared spectroscopy utilizing iron oxide coated internal reflection elements to enhance the limits, Analytica Chimica Acta, vol. 581, 2007, pp. 309-317.*

Bernardo, G. et al., "Role of Ettringite in the Reuse of Hydrated Fly Ash from Fluidized-Bed Combusion as a Sulfur Sorbent: A Hydration Study," Ind, Eng. Chem. Res., 43, 2004, pp, 4054-4059.

Hiraga, Y., "Boron Uptake Behavior During Ettringite Synthesis in the Presence of H3BO3 and in a Suspension of Ettringite in H3BO3," Journal of Chemical Engineering of Japan, vol. 43, No. 10, 2010, pp. 865-871.

Janneck, E. et al., "Ettringite Precipitation vs. Nano-filtration for Efficient Sulphate Removal from Mine Water," International Mine Water Association Annual Conference, edited by McCullough Lund and Wyse, 2012, pp. 206I-206R.

Zhang, M . et al., "Removal of B, Cr, Mo, and Se from Wastewater by Incorporation into Hydrocalumite and Ettringite," Environ. Sci. Technol., 37, 2003, pp. 2947-2952.

International Search Report and Written Opinion mailed Jun. 8, 2015 for related International Application PCT/US2014/054390, 14 pages.

International Search Report mailed May 26, 2014 for related International Application PCT/US2014/014948, 3 pages.

(Continued)

*Primary Examiner* — Christine T Mui

(74) *Attorney, Agent, or Firm* — Fredrikson & Byron, P.A.

(57) ABSTRACT

To determine the concentration of an oxoanion in an aqueous solution, an aluminum reagent is added to the aqueous solution to form an optical analysis solution. Addition of the aluminum reagent may or may not form an alumino-oxoanion hydroxide hydrate precipitate. Light is directed into the optical analysis solution to determine an optical response of the optical analysis solution. Thereafter, the concentration of the oxoanion in the aqueous solution is determined based on the optical response of the optical analysis solution. For example, the concentration of the oxoanion may be calculated using a molar ratio relating oxoanion concentration to aluminum reagent concentration, when the aluminum reagent concentration corresponds to an inflection point of the optical response of the optical analysis solution.

33 Claims, 17 Drawing Sheets

(56) References Cited

OTHER PUBLICATIONS

International Search Report and Written Opinion mailed Jun. 8, 2015 for related International Application PCT/US2014/054396, 23 pages.

Butseva et al., "Removal of Sulfates From Wastewater by Liming and Coagulation and Using Aluminum Oxychloride," Abstract, Vodosnabzhenie i sanitarnai•a• tekhnika, 2009, pp. 49-51.

Cheng et al., "Study on Removal of Sulfuric Acid Radical From Mining Water," Abstract, Wujiyan Gongye, vol. 41, Issue 7, 2009, pp. 51-53.

Lin, "Treatment of Sulfate Wastewaters," Abstract, Tumu Shuili, vol. 9, Issue 3, 1982, pp. 25-31.

Rubio et al., "Clean Technologies for the Treatment of Coal Acid Mining Effluents," Fifth International Conference on Clean Coal Technologies, Zaragoza, Spain, 2011, pp. 1-11.

Smit et al., "Pilot Plant Study to Treat Typical Gold Mine Minewater Using the Savmin Process," Water in Mining, vol. 6, 2003, pp. 355-362.

Hubbe, "Polyaluminum Chloride (PAC)," Mini-Encyclopedia of Papermaking Wet-End Chemistry, NC State University, Feb. 1, 2001.

* cited by examiner

OXOANION CONCENTRATION DETERMINATION USING ALUMINUM REAGENTS

This application may be found related to U.S. patent application Ser. No. 13/787,365, filed Mar. 6, 2013, and U.S. patent application Ser. No. 14/478,946, filed Sep. 5, 2014. The entire contents of both these applications are incorporated herein by reference.

TECHNICAL FIELD

This disclosure relates to the quantification of oxoanions and, more particularly, to the quantification oxoanions in aqueous solutions having unknown concentrations of oxoanions.

BACKGROUND

Oxoanions are a class of oxygen-bearing anionic molecules that can be formed during industrial processes. Typical oxoanions encountered during commercial processing operations include borate, carbonate, phosphate, sulfate, chromate, and arsenate. These oxoanions can be formed when a substance containing the non-oxygen element of the oxoanion is exposed to oxygen, water, and/or bacteria. For example, during excavation of earthen material, such as mining and milling operations, minerals in rocks can be exposed to oxidizing conditions forming oxoanions in water seepages or process waste streams.

Because of the adverse health and environmental effects associated with many oxoanions, governmental regulatory agencies often limit the level at which certain oxoanions can be discharged with waste water into the environment. As a result, process operators and manufacturing sites generating oxoanions often desire to monitor the concentration of oxoanions present in process streams, such as waste water streams being released to the environment. Oxoanion concentration information can also be used to establish or adjust a treatment regime intended to reduce the concentration of oxoanions present in a stream before being discharged to the environment.

In practice, oxoanion compositions and concentrations can change over time and with environmental factors. Factors such as rainfall, temperature, industrial process conditions, earthen matter content, and process chemical components can cause changes in the makeup of oxoanions in a given waste water stream over time. Ensuring that the oxoanion concentration in an aqueous stream is accurately and timely measured can help ensure compliance with governmental regulatory requirements and good environmental and health stewardship.

SUMMARY

In general, this disclosure is directed to devices, systems, and techniques for optically determining the concentration of an oxoanion in an aqueous solution having an unknown oxoanion concentration using an aluminum-based reagent. In some examples, the technique involves adding an aluminum reagent to the aqueous solution to form an alumino-oxoanion particulate that changes the optical properties of the aqueous solution. For example, addition of the aluminum reagent to the aqueous solution may form an alumino-oxoanion hydroxide hydrate precipitate that is held in suspension within the aqueous solution under observation. The optical response of the aqueous solution may vary depending on the extent and characteristics of the precipitate formed which, in turn, can vary depending on the concentration of the oxoanion present in the aqueous solution. By optically analyzing the aqueous solution after addition of the aluminum reagent, the optical response of the solution can be used to determine the concentration of the oxoanion present in the solution.

Without wishing to be bound by any particular theory, it is believed that the aluminum reagent may hydrolyze upon addition to the aqueous solution to form an Al Keggin ion-type structure. The resulting structure may be an oligomeric species that incorporates one or more oxoanion molecules into the oligomeric structure. The oligomeric species may absorb and/or reflect light directed into the aqueous solution in proportion to the concentration of the oligomeric species present in the solution. Further, the concentration of the oligomeric species may vary depending on the concentration of the oxoanion present in the aqueous solution. As a result, the concentration of the oxoanion present in the aqueous solution can be determined based on the optical response of the aqueous solution after addition of the aluminum reagent.

In practice, it has been observed in some examples that the optical response of an aqueous solution containing oxoanion species is predictable (e.g., generally linear, curved, exponential) within a given concentration range at a specific aluminum concentration but is non-predictable outside of that range. In instances where an aqueous solution has an unknown oxoanion concentration that is expected to be within the given concentration range, a predetermined amount of aluminum reagent may be added to the aqueous solution corresponding to an amount used to develop the predictable (e.g., generally linear, curved, exponential) calibration information. The oxoanion concentration in the aqueous solution can be determined by correlating the optical response of the solution to the oxoanion concentration using the calibration information.

In other applications where the unknown oxoanion concentration is not expected to be within a given concentration range, the oxoanion concentration may be determined by sequentially adding portions of aluminum reagent to the aqueous solution, thereby progressively increasing the amount of aluminum reagent added to the solution. The optical response of the aqueous solution can be determined after each portion of aluminum reagent is added to the aqueous solution. In some examples, an optical inflection point (e.g., minima or maxima) is observed when the concentration of the oxoanion is at a specific molar ratio or range of molar ratios relative to the aluminum concentration. Accordingly, the oxoanion concentration can be determined based on the amount of aluminum reagent corresponding to the inflection point of the optical response and the known molar ratio relating oxoanion concentration to aluminum concentration at that location.

In some applications, a fluorophore is added to the aqueous solution having the unknown concentration of oxoanions to determine the oxoanion concentration based on fluorometric response. In practice, it has been observed in some examples that emission intensity of the fluorophore decreases with increasing oxoanion concentration (at a fixed aluminum concentration) up to an oxoanion concentration inflection point, whereupon the fluorophore emission intensity begins increasing with continued increasing oxoanion concentration. Without again wishing to be bound by any particular theory, it is believed that the fluorophore species and oxoanion species may both compete to react with the aluminum present within the aqueous solution. For example, an Al Keggin ion-type structure may form upon addition of the aluminum to the aqueous solution, creating an oligomeric species that incorporates one or more oxoanion molecules and/or fluorophore molecules. The extent of fluorophore incorporation into the oligomer (and hence corresponding decrease in fluorescent emission response) is related to the oxoanion concentration in the solution, among other factors, allowing quantification of the oxoanion concentration.

In one example, a method is described that includes adding an aluminum reagent to an aqueous solution having an unknown concentration of an oxoanion and thereby forming an optical analysis solution comprising an alumino-oxoanion hydroxide hydrate precipitate. The method further includes directing light into the optical analysis solution and determining therefrom an optical response of the optical analysis solution, and determining a concentration of the oxoanion in the aqueous solution having the unknown concentration of the oxoanion based on the optical response of the optical analysis solution.

In another example, a system is described that includes a source of an aqueous solution having an unknown concentration of an oxoanion and an aluminum reagent source configured to supply aluminum reagent to the aqueous solution and thereby form an optical analysis solution comprising an alumino-oxoanion hydroxide hydrate precipitate. The system also includes an optical sensor including an emitter configured to direct light into the optical analysis solution and a detector configured to detect light from the optical analysis solution and provide therefrom an optical response. The system also includes a controller configured to determine a concentration of the oxoanion in the aqueous solution having the unknown concentration of the oxoanion based on the optical response of the optical analysis solution.

The details of one or more examples are set forth in the accompanying drawings and the description below. Other features, objects, and advantages will be apparent from the description and drawings, and from the claims.

DETAILED DESCRIPTION

Figure 1:
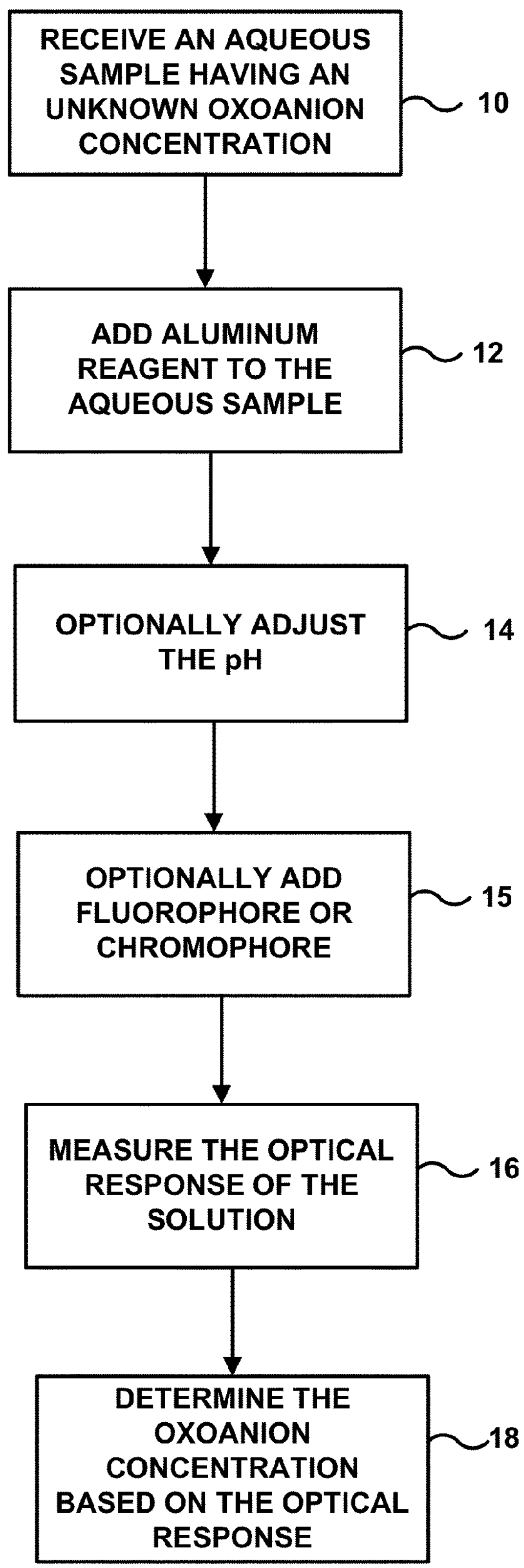
FIG. 1 is a flow diagram illustrating an example process for optically measuring oxoanion concentration using an aluminum-based reagent.

This disclosure generally relates to techniques and systems for measuring oxoanion concentrations in water-based liquids using aluminum reagents. In some examples, a sample of a liquid containing an unknown oxoanion concentration is extracted from a source and an aluminum reagent is added to the sample. The aluminum reagent may be homogeneously mixed throughout the sample to provide a medium intended for subsequent optical analysis and referred to as an optical analysis solution. The optical analysis solution may be optically analyzed by directing light into the solution and detecting light from the solution, thereby providing an optical response of the optical analysis solution. In different examples, the light detected from the solution may be light transmitted through the solution or scattered by solids present in the solution (providing a transmittance and/or absorbance optical response, or colorimetric optical response in cases where an optically absorbing chromophore is present), light reflected or scattered by the solution (providing a turbidity optical response), and/or fluorescent light emanating from the solution in response to the emitted light (providing a fluorescence optical response). In any example, the optical response may vary depending on the concentration of oxoanion in the sample and, accordingly, the oxoanion concentration can be determined based on the optical response.

For example, upon addition of an aluminum reagent to an oxoanion containing aqueous sample, at least a portion of the aluminum reagent may hydrolyze to form an alumino-hydroxide particulate/precipitate that changes the optical properties of the aqueous solution containing the oxoanion. The alumino-hydroxide particulate may be an oligomeric or polymeric network structure that incorporates one or more oxoanion species into the structure, e.g., via electrical attraction forces or covalent bonding. The amount of particulate formed can vary, for example, depending on factors such as the chemical composition of the oxoanions in the aqueous sample, the concentration of the oxoanion, the amount of aluminum introduced into the aqueous sample, and the pH of the sample. Because the particulate changes the optical characteristics of the aqueous sample as compared to the optical characteristics prior to introduction of the aluminum reagent, the optical response of the aqueous sample containing added aluminum reagent can be used to quantify the amount of oxoanion in the sample.

Measuring oxoanion concentrations in aqueous samples can be useful for a variety of reasons. Process streams may be subject to various oxoanion concentration limits, such as limits on the amount of oxoanions that can be discharged to the environment with waste water or the amount of oxoanions that can be present in a process stream because of downstream processing requirements. Accordingly, optical analysis of samples from the process streams can provide oxoanion concentration compliance tracking information. As another example, oxoanion concentration measurement information can provide control information that can be used to control oxoanion treatment and removal processes. For example, oxoanion concentration information generated according to the present disclosure can be used to control dosing of precipitating agents added to precipitate out and remove oxoanions from a stream undergoing treatment. An example technique for treating aqueous streams containing oxoanions is described in a co-filed patent application entitled "ADDITION OF ALUMINUM REAGENTS TO OXOANION-CONTAINING WATER STREAMS" and assigned Ser. No. 14/478,946, the entire contents of which are incorporated herein by reference.

Ensuring that the oxoanion concentration in an aqueous sample undergoing evaluation is accurately and timely quantified can help control treatment regimens and ensure compliance with any concentration limits placed on the underlying sample source. Depending on the desired application, the disclosed systems and techniques can be implemented as an on-line monitoring tool to automatically determine and record the oxoanion concentration in a process stream. The oxoanion concentration information determined by the online monitoring tool can then be used to automatically control other aspects of the process, such as waste water discharge, oxoanion precipitating agent dosing, and the like.

FIG. 1 is a flow diagram illustrating an example process for optically measuring oxoanion concentration using an aluminum-based reagent. The example process includes receiving a sample of an aqueous solution having an unknown oxoanion concentration (10) and adding an aluminum-based reagent to the sample (12), thereby forming an optical analysis solution. The example process also includes optionally adjusting the pH of the solution (14) and/or optionally adding a fluorophore or chromophore to the aqueous sample undergoing analysis (15). Additionally, the example process further includes measuring the optical response of the optical analysis solution (16) and determining the concentration of the oxoanion in the aqueous solution based on the optical response (18). As described in greater detail below, the optical response of optical analysis solution may vary based on factors such as the composition and amount of aluminum-based reagent added to the sample, the concentration and chemical composition of the oxoanions in the aqueous sample, and the pH of the sample. By appropriately controlling addition of the aluminum-based reagent and processing of the optical response data, the concentration of the oxoanions present in the aqueous solution can be extracted from the optical response data.

In the technique of FIG. 1, an aqueous solution having an unknown oxoanion concentration is received from a source (10). The aqueous solution can be received from a variety of different industrial processes, and the disclosure is not limited to treating an aqueous solution from any particular source. In some applications, the aqueous solution is a sample from a discharge stream, effluent, run-off, and/or seepage from a mine, coal refuse pile, construction site, chemical plant, or other location. For example, the aqueous solution may be a discharge stream forming a mine drainage where rock formations have been disturbed (e.g., excavated) and exposed to water sources such as rainfall, surface water, and/or subsurface water sources, such that the water contains metals and minerals in solution or suspension. Such a stream can be produced from mine sites, including active, inactive, or abandoned extraction and/or excavation operations for removing minerals, metals, ores and/or coal from the earth. Examples of such extraction operations include oil sands, coal, minerals, metals and ores including limestone, talc, gold, silver, iron, zinc, manganese, molybdenum, antimony, chromium, copper, and nickel.

Independent of the source of the aqueous solution, the solution may contain oxoanions at an unknown concentration (e.g., a concentration that is undetermined by an external user). The term oxoanion, which may also be called an oxoanion, refers to a negatively charged chemical compound having the formula $A_xO_y^{z-}$, where A is a chemical element other than oxygen; O is oxygen; Z is typically an integer having a value of at least 1 (e.g., 1, 2, 3, or more); X is typically an integer having a value of 1 or 2; and Y is typically an integer having a value of at least 1 (e.g., 1, 2, 3, 4, or more).

Oxoanions can be formed by many chemical elements. For example, oxoanions include borate, carbonate, nitrate, phosphate, sulfate, chromate, arsenate, selenate, molybdate, nitrite, phosphate, sulfite, arsenite, selenite, hypophosphite, phosphate, hyposulfite, perchlorate, perbromate, periodate, permanganate, chlorate, chromate, bromate, iodate, chlorite, bromite, hypochlorite, and hypobromite. A specific oxoanion can be formed at an extraction site by exposing a chemical element to oxygen and water. For example, the oxoanion sulfate can be formed when extracted earthen material containing metal sulfide is exposed to oxygen and water.

The specific oxoanions present in the aqueous solution undergoing analysis will vary, e.g., based on the type of process producing the solution and the source of the oxoanions. In some examples, the aqueous solution undergoing analysis includes (or, in other examples, consists or consists essentially of) sulfate, molybdate, borate, selenate, selenite, arsenate, nitrate, and/or vandinate. For example, the aqueous stream may have one or more oxoanions having the formula $A_xO_y^{z-}$, where A is selected from the group consisting of Mo, B, Cr, Se, Ar, N, and S; X is an integer having a value of 1 or 2; Y is an integer having a value 2, 3, or 4, and Z is an integer having a value of 1, 2, or 3. In one specific example, the aqueous solution includes (or, in other examples, consists essentially of) sulfate ($SO_4^{2-}$). Sulfate is an oxoanion found in many mine rock drainage waste streams and other excavation effluents. In some examples, the aqueous stream includes a mixture of multiple oxoanions.

As another example, the aqueous solution undergoing analysis may include sulfate as the oxoanion and/or oxoanions that are isostructural with sulfate and have a negative charge of −2 or greater. For example, the aqueous solution may include an oxoanion having the formula $A_xO_y^{z-}$, where A is a chemical element selected from the group consisting of Se, P, As, Cr, B, Mo, V, and S; X is an integer having a value of at least 1 (e.g., 1 or 2); O is oxygen; Y is an integer having a value of at least 1 (e.g., 1, 2, 3, 4, or more); and Z is an integer having a value of 2 or greater. Examples of such oxoanions include selenite, phosphate, arsenate, chromate, molybdate, and vanadate. Sulfate and oxoanions isostructural with sulfate have been observed to network with Al Keggin ion-type structures that may form upon addition of aluminum to an aqueous solution containing the oxoanions. As a result, optically active or interfering particles incorporating the oxoanions in the Al Keggin ion-type structures can be optically measured to determine the concentration of oxoanions in the sample under analysis.

In addition to containing one or more oxoanions, the aqueous solution undergoing analysis may contain corresponding cations, e.g., providing electrical charge neutrality to the solution. The types of cations present in the aqueous solution will again vary based on the process producing the solution and the source of the cations. Typical cations associated with oxoanion-containing waste effluent solution include metal cations, such as Group I alkali metals (e.g., Na, K) and/or Group II alkaline earth metals (e.g., Be, Mg, Ca). In the case of mine rock drainage solutions, heavy metals such as iron, chromium, cobalt, zinc, nickel, and/or copper may also be present.

The technique of FIG. 1 is not limited to analyzing aqueous solutions having any particular oxoanion concentration range. For example, the concentration of oxoanions in the aqueous solution under evaluation, while initially unknown, can range, e.g., from less than 500 parts per million (ppm) to greater than 1000 ppm. For example, the oxoanions in the solution may be greater than 500 ppm, such as greater than 750 ppm, greater than 1000, greater than 1500 ppm, greater than 2500 ppm, or greater than 10,000 ppm (e.g., 10,000 ppm to 20,000 ppm). In some applications, the concentration of the oxoanions in the aqueous solution may be less than 3000 ppm, such as less than 2500 ppm, or less than 2000 ppm. For example, the concentration of the oxoanions in the aqueous solution may range from 10 ppm to 2500 ppm, such as from 50 ppm to 2000 ppm, or from 500 ppm to 1500 ppm. It should be appreciated that the foregoing concentrations are merely examples and the disclosure is not limited in this respect. Further, unless otherwise noted, parts per million (ppm) as used herein referred to parts per million by weight.

Depending on the source of the aqueous solution, the concentration of the oxoanions may vary over time (e.g., such that a sample of aqueous solution taken from the source at one time may have a different oxoanion concentration than a sample of aqueous solution taken from the source at a different time). Factors such as rainfall, temperature, industrial process conditions, and earthen matter content, among others, can cause the oxoanions to become diluted or increase in concentration in a flowing stream relative to the concentration at an earlier period of time. The concentration change of the oxoanion over a period of time may be greater than 10 percent, such as greater than 25 percent, or greater than 50 percent. The period of time over which the concentration varies may be comparatively short, such as a half hour or hour, or longer, such as a shift (e.g., an eight hour shift), a day, or a week.

In addition to one or more oxoanions and corresponding metal cations, the remainder of the stream may comprise water and specific compounds corresponding to the source of the aqueous stream. Example compounds that may be present in the aqueous stream include, but are not limited to, transitional metal cations, carbonated bicarbonate, cyanide, organics, flocculants, and/or floatation aids.

Regardless of the composition of the aqueous solution being received, the solution can be received from a source and subject to optical analysis to determine oxoanion content (10). The aqueous solution can be received and collected within an optical analysis vessel (e.g., an optical cell), providing a static volume of liquid that can be analyzed. Alternatively, the aqueous solution can be analyzed continuously (e.g., by drawing a slip stream), adding aluminum reagent to the flowing stream, and optically analyzing the stream as it flows past an optical sensor.

In the example technique of FIG. 1, the aqueous solution having an unknown concentration of oxoanion is received (10) and an aluminum-based reagent is added to the aqueous solution (12) thereby forming an optical analysis solution. In different examples, the aluminum-based reagent can be added to a static vessel containing the aqueous solution or a flowing stream of the aqueous solution. The aluminum-based reagent may or may not be mixed (e.g., homogenously) with the aqueous solution to uniformly distribute the reagent throughout the aqueous solution. In either case, the aluminum reagent can react with the aqueous solution to form an aluminum-based particulate or precipitate in the optical analysis solution. For example, the aluminum-based reagent may hydrate upon addition to the aqueous solution forming an aluminum-hydroxide-hydrate particulate or precipitate.

Although not intending to be limited to any particular theory of operation, it is believed that the aluminum-based reagent may hydrolyze upon addition to the aqueous solution to form an aluminum Keggin ion structure type. The aluminum Keggin ion is an alumino-hydroxide-hydrate oligomer structure having the general formula $[Al_{13}O_4(OH)_{24}.2H_2O]^{7+}$. The $Al_{13}$ aluminum form has a cluster structure in which octahedral sites are associated with tetrahedral sites, the tetrahedral sites representing about 1% to 20% of the sites, usually about 6% to 10% of the sites. The positive charge on the aluminum Keggin ion species can incorporate negatively charged species (e.g., oxoanions, fluorophores, chromophores) into the oligomeric network via intermolecular charge attraction forces (e.g., van der Waals forces). As a result, the extent to which the aluminum-hydroxide-hydrate species forms and the optical properties of the particulate or precipitate can vary depending on the concentration of negatively charged oxoanions present in the aqueous solution.

Any suitable source of aluminum can be used as the aluminum-based reagent. The aluminum reagent may be basic such that addition of the aluminum reagent to the aqueous solution increases the pH of the solution, acidic such that addition of the aluminum reagent to the aqueous solution reduces the pH of the solution, or substantially pH neutral. Example aluminum reagents include, but are not limited to, alum (aluminum sulfate), sodium aluminate, calcium aluminate, aluminum chloride, polyaluminum chloride, aluminum hydroxide, aluminum acetate, aluminum nitrate, and fly ash. In some examples, the aluminum reagent is a water-soluble salt, such as an aluminum chloride.

The amount of aluminum-based reagent added to the aqueous solution (12) can vary, e.g., depending on the quantity of aqueous solution undergoing treatment and the type of oxoanion present within the aqueous solution. In practice, an optical analysis solution may exhibit a predictable and repeatable optical response (e.g., generally linear, curved, exponential) with increasing concentration within a given concentration range at a particular aluminum dosing but non-predictable behavior outside of that range. For example, in instances where the oxoanion is or includes sulfate, the optical analysis solution may exhibit a generally linear response with increasing concentration within a given range. While the range may vary, for example based on the amount of aluminum added to the aqueous solution, in some examples, the range is from 100 ppm oxoanion to 4000 ppm oxoanion, such as from 250 ppm oxoanion to 3000 ppm oxoanion, or from 1000 ppm oxoanion to 2000 ppm oxoanion.

Figure 2:
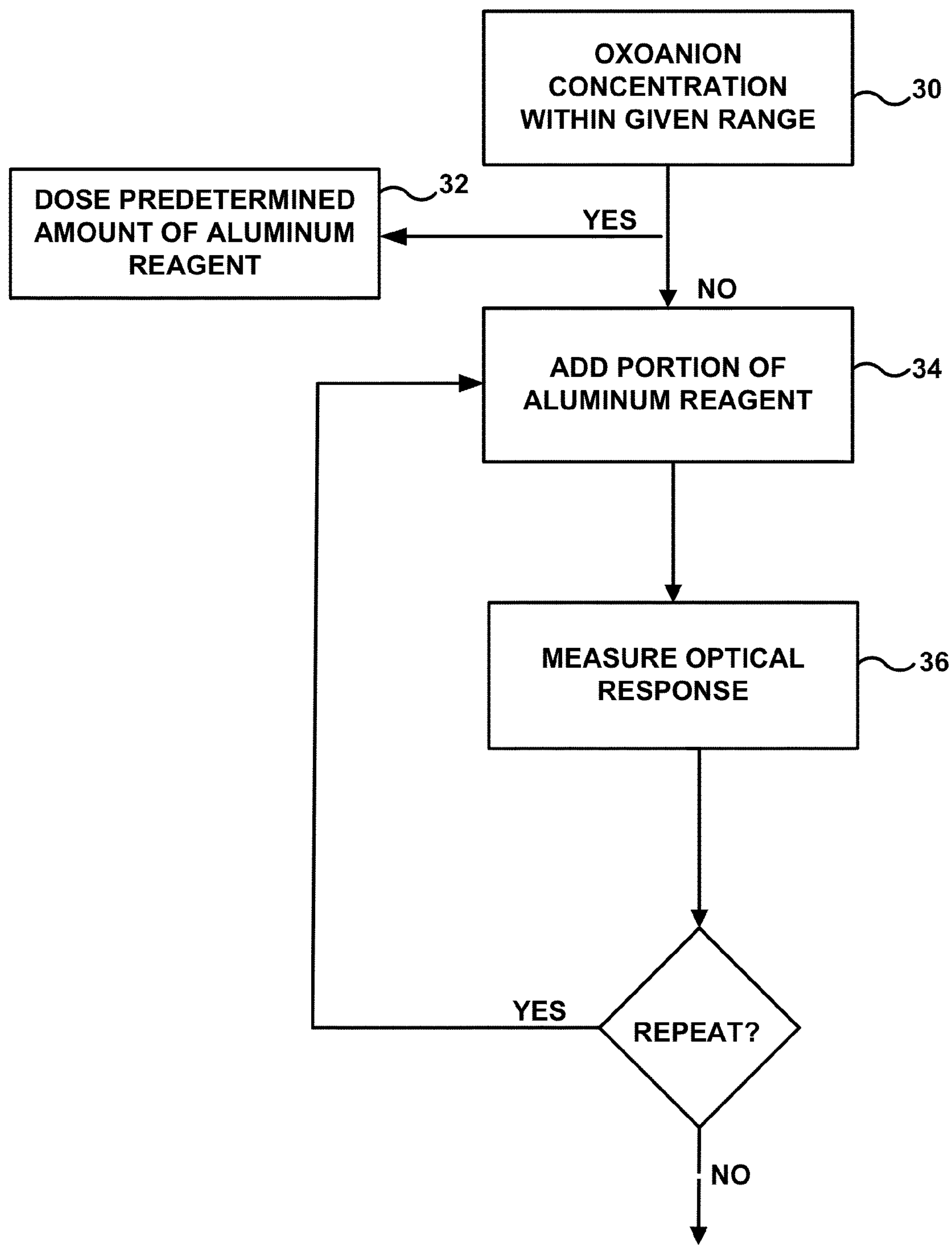
FIG. 2 is a flow diagram showing an example process for controlling aluminum addition based on the characteristics of the aqueous solution under analysis for the technique of FIG. 1.

FIG. 2 is a flow diagram showing an example process for controlling aluminum addition based on the characteristics of the aqueous solution under analysis. As shown in this example, in instances where the aqueous solution is expected to have an oxoanion concentration within a range providing a predictable and repeatable optical response (30) (e.g., linear, curved, exponential), a predetermined amount of aluminum-based reagent may be added to the aqueous solution. The oxoanion concentration may be expected to be within a concentration range providing a predictable and repeatable optical response based on prior analysis of aqueous samples from the same source as the aqueous solution currently undergoing analysis and the consistency of oxoanion concentration values previously observed from the source. If the aqueous solution is expected to have an oxoanion concentration within a range providing a generally predictable and repeatable optical response (30) (e.g., as would be expected by an individual controlling aluminum reagent dosing or programming of a machine to provide such dosing), a predetermined amount (e.g., fixed amount) of aluminum reagent can be added to the aqueous solution (32). An aqueous solution may exhibit a generally predictable and repeatable optical response of a certain characteristic, such as linear, if a plot of optical response (e.g., in turbidity units, absorbance units, fluorescence emission intensity units) versus oxoanion concentration over a range of different oxoanion concentrations is generally linear. The predetermined amount may be an amount used previously to generate calibration information relating optical responses of aqueous solutions having known oxoanion concentrations to those oxoanion concentrations, when using the predetermined amount of aluminum reagent.

For example, if the predetermined amount of aluminum reagent is 50 ppm aluminum, the calibration information can relate optical responses of aqueous solutions having different known oxoanion concentrations (e.g., ranging from oxoanion concentrations of 5 ppm to 5000 ppm) to those oxoanion concentrations, as measured after adding 50 ppm aluminum to each of the aqueous solutions having different known oxoanion concentrations. In various examples, the predetermined amount of aluminum may range from 5 ppm aluminum to 500 ppm aluminum, although other amounts can be used without departing from the scope of the disclosure. As an example (e.g., when the optical response is linear), the concentration of aluminum may be determined by dividing the weight of aluminum added to the solution (excluded the weight of other aluminum reagent atoms) by the total weight of the solution.

In instances where there is no expectation regarding the oxoanion concentration in the aqueous solution or the oxoanion concentration is expected to be outside a concentration range providing a repeatable optical response, progressively increasing amounts of aluminum reagent may be added to the aqueous solution (34) instead of a single predetermined amount. For example, a portion of aluminum-based reagent can be added to the aqueous solution (34) and the optical response of the solution thereafter determined (36). The process can be repeated (38) with additional portions of aluminum-based reagent being added to the aqueous solution and additional optical responses being determined until an optical inflection point (e.g., minima or maxima) is observed. The optical inflection point may be a minima when the optical response being measured is absorbance or fluorescence and a maxima when the optical response being measured is turbidity.

Each portion of aluminum-based reagent added to the aqueous solution (34) may be the same size (e.g., volume or weight) as each other portion of aluminum-based reagent added to the solution, or at least one portion of aluminum-based reagent may have a different size (e.g., smaller or larger) than at least one other portion of aluminum-based reagent added to the solution. In some examples, each portion of aluminum-based reagent ranges from 5 ppm aluminum to 50 ppm aluminum, although other amounts can be used.

At the aluminum concentration corresponding to the optical inflection point or approximately thereabout, the concentration of the oxoanion may be at a specific molar ratio or range of molar ratios relative to the aluminum concentration. Depending on the type of oxoanion present in aqueous solution, the concentration of the oxoanion may range from ten moles of oxoanion per one mole of aluminum to one mole of oxoanion per ten moles of aluminum, when the aluminum reagent is at or near the inflection point of the optical response, such as from one mole of oxoanion per two moles of aluminum to one mole of oxoanion per ten moles of aluminum. For example, in the case of the oxoanion sulfate, the concentration of the oxoanion may range from one mole of oxoanion per three moles of aluminum to one mole of oxoanion per six moles of aluminum, when the aluminum reagent is at or near the inflection point of the optical response, such as from one mole of oxoanion per 3.2 moles of aluminum to one mole of oxoanion per 5 moles of aluminum, or approximately one mole of oxoanion per 3.7 moles of aluminum.

The following table provides a listing of example oxoanion to aluminum molar ratios for different oxoanion species, as may be present when the aluminum dose corresponds to an optical inflection point.

| Example Oxoanion | Example Inflection Point Response Range (mol Al/mol oxoanion) | Example mol Al/mol Oxoanion at an Emission Minima | Example mol Al/mol Oxoanion at a Turbidity Maxima |
|---|---|---|---|
| Sulfate | 3-6 | 3.7 (e.g., at a lower concentration range, such as 1-200 ppm $SO_4$) 4.9 (e.g., at a higher concentration range, such as 10-2000 ppm $SO_4$) | 3.7 |
| Molybdate | 5-9 | 5.9 | 5.9 |
| Chromate | 8-10 | | 9.3 |
| Selenate | 1-6 | 1.8 | |
| Arsenate | 2-6 | 5.1 | |
| Borate | 1-3 | 1.4 | |

With further reference to FIG. 1, the example technique also includes optionally adjusting the pH of the optical analysis sample (14) prior to optically analyzing the sample (16). The pH may be adjusted prior to, concurrent with, or after adding the aluminum-based reagent to the aqueous sample. As discussed above, an aluminum-based reagent can be added to the aqueous solution undergoing analysis to form an aluminum-hydroxide-hydrate particulate or precipitate that changes the optical properties of the solution. Formation of this particulate or precipitate may be pH dependent such that the particulate or precipitate does not form or does not form strongly if the pH is too high or too low. Accordingly, in some examples, the pH of the aqueous solution may be pH adjusted to a pH effective to form the aluminum-hydroxide-hydrate particulate or precipitate. For example, the pH may be adjusted to a pH below 8 such as below 7, or a range from approximately 3 to approximately 6, such as approximately 4.5. Depending on the pH of the source of the aqueous solution, the pH may be increased by adding a base to the solution or reduced by adding an acid to the solution to bring the pH within a desired range. In one example, the pH is adjusted with a weak organic acid, such as acetic acid.

The technique of FIG. 1 also includes optionally adding a fluorophore and/or chromophore to the aqueous sample undergoing analysis (15). As with the optional pH adjustment step, the fluorophore or chromophore may be added to the aqueous sample prior to, concurrent with, or after adding the aluminum-based reagent to the aqueous sample. Addition of the fluorophore or chromophore may enhance the optical response of the optical analysis solution, helping to increase the accuracy and/or range of oxoanion concentrations that can be optically measured. The optical analysis solution (e.g., comprising an aqueous oxoanion solution, an aluminum-based reagent, and/or pH adjusting agent) may not exhibit any fluorescence or may exhibit only minimal fluorescence that does not correspond to the concentration of oxoanions in the solution. The fluorophore may interact with oxoanions and/or other species in the optical analysis solution to provide a fluorescence emission response, the magnitude of which varies based on the oxoanion concentration present in the optical analysis solution. Similarly, the chromophore may interact with oxoanions and/or other species in the optical analysis solution to provide an absorption response, the magnitude of which varies based on the oxoanion concentration present in the optical analysis solution.

For example, in practice, it has been observed in some examples that emission intensity of the fluorophore decreases with increasing oxoanion concentration (at a fixed aluminum concentration) up to an oxoanion concentration inflection point, whereupon the fluorophore emission intensity begins increasing with continued increasing oxoanion concentration. Without wishing to be bound by any particular theory, it is believed that the fluorophore species and oxoanion species may both compete to react with the aluminum present within the aqueous solution. For example, an Al Keggin ion-type structure may form upon addition of the aluminum to the aqueous solution, creating an oligomeric species that incorporates one or more oxoanion molecules and/or fluorophore molecules, e.g., via intermolecular charge attraction forces (e.g., van der Waals forces). It is further believed that the fluorophore molecules incorporated into the Al Keggin ion-type structure do not exhibit a fluorescent response (or diminished fluorescent response). Accordingly, relative competition between the oxoanion molecules and fluorophore molecules for the aluminum present in the solution causes the fluorescence emissions response of the fluorophore to vary depending on the concentration of oxoanions present. In other words, at a given fluorophore dosing, the optical analysis solution may exhibit a fluorescence emission intensity of a given magnitude when the oxoanions are at a given concentration but a different magnitude when the oxoanions are at a different concentration. Chromophores can be expected to exhibit similar Al Keggin ion-type structure incorporation and optical response behavior.

When used, any fluorophore that interacts with (e.g., binds) aluminum (e.g., to form an alumino-fluorophore hydroxide hydrate precipitate or particulate) to provide an emission response that varies based on oxoanion concentration can be used. As used herein, the term "fluorophore" refers to a composition of matter which emits fluorescent light when irradiated with light of an appropriate wavelength and includes, but is not limited to, fluorescent: dyes, pigments, polymers, metal ions, metal complexes, and any combination thereof.

In some examples, the fluorophore includes one or more anionic pendant groups (e.g., 2, 3, 4 or more), which may be effective to interact and bind with an alumino-hydroxide-hydrate oligomer present in the aqueous solution undergoing evaluation. Example anionic pendant groups that can be used include carboxylate, sulfonate, sulfate, alcohol, and phosphate groups.

In some examples, the fluorophore may include (or be selected from the list consisting of): 1,3,6,8-pyrenetetrasulfonic acid and salts thereof, 1-pyrenesulfonic acid and salts thereof, 1-pyrenecarboxylic acid and salts thereof, 1-pyreneacetic acid and salts thereof, 1-methylaminopyrene and salts thereof, 8-hydroxy-1,3,6-pyrenetrisulfonic acid and salts thereof, 1-aminopyrene and salts thereof, y-oxo-1-pyrenebutyric acid and salts thereof, 1-naphthalenesulfonic acid and salts thereof, 2-napthalenesulfonic acid and salts thereof, 4-hydroxy-1-naphthalenesulfonic acid and salts thereof, 1,5-naphthalenedisulfonic acid and salts thereof, 1-amino-5-naphthalenesulfonic acid and salts thereof, 6,7-dihydroxy-2-naphthalenesulfonic acid and salts thereof, 6-hydroxy-2-naphthalenesulfonic acid and salts thereof, 1-hydroxy-2-naphthoic acid and salts thereof, 2-hydroxy-1-naphthoic acid and salts thereof, 3-hydroxy-2-naphthoic acid and salts thereof, 2,6-naphthalenedicarboxylic acid and salts thereof, 1-naphthylacetic acid and salts thereof, 1-naphthoxylactic acid and salts thereof, 1-naphthoxyacetic acid and salts thereof, 2-naphthoxyacetic acid and salts thereof, 1-naphthalenephosphonic acid and salts thereof, 1-aminonaphthalene and salts thereof, N-allyl-4-(2-N',N'-dimethylaminoethoxy) naphthalimide methyl sulfate quaternary salt, 4-chloro-2-phenyleiminomethylphenol, N,N'-disalicylidene-1,3-diamino-2-hydroxypropane, SOM fluorescent compound, a polymer containing an SOM fluorescent compound, GQW polymer (red), GQW polymer (purple), and any combination thereof.

As used herein, the term "SOM Fluorescent Compound" means a fluorescent compound as described in U.S. Pat. No. 6,358,746 (incorporated herein by reference) of the formula:

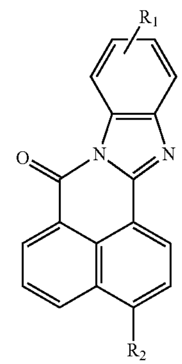

wherein R1 and R2 are either both $SO_3M$, or one of R1 and R2 is $SO_3M$ and the other is COOM, where M is selected from the group consisting of H, Na, K, Rb, Cs, Li or ammonium.

As used herein, the term "GQW Polymer (Red)" means a tagged treatment polymer as described in U.S. Pat. No. 6,645,428 (incorporated herein by reference) selected from the group consisting of: GaQjWt (1) wherein G is selected from the group consisting of:

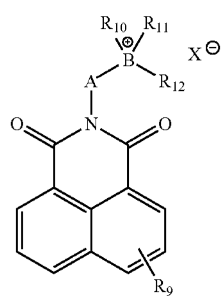

wherein R9 is selected from the group consisting of hydrogen, alkyl, alkoxy, halogen, sulfonic acid and its salts, phosphonic acid and its salts, dialkylamino, allyloxy and vinylbenzyloxy; R10 and R11 are alkyl; R12 is selected from the group consisting of allyl, 2-hydroxy-3-allyloxy-propyl, vinylbenzyl, 3-methacrylamidopropyl, 3-acrylamidopropyl, 2-acryloxyethyl and 2-methacryloxyethyl; A is selected from the group consisting of alkyl, alkoxyalkyl, alkylamidoalkyl, aryl or nonexistent; with the proviso that when A is nonexistent, B is nitrogen (N) and B is bonded directly to the imide nitrogen; B is sulfur or nitrogen with the proviso that when B is sulfur only one of R10 or R11 is present; and X is an anionic counter ion; wherein Q is selected from the group consisting of acrylic acid and salts thereof, methacrylic acid and salts thereof, maleic acid and salts thereof, maleic anhydride, acrylamide, crotonic acid, acrylamidomethylpropane sulfonic acid and salts thereof; wherein W is selected from the group consisting of: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, Nisopropylacrylamide, butoxymethylacrylamide, N,N-dimethylacrylamide, N,Ndiethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylamninopropy acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, triallylamine, acid salts of trial lylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, and N-vinylpyrrolidone; with the proviso that Q and W cannot both be the same; wherein a is from about 0.001 to about 10.0 mole percent; wherein j is from about 0 to about 99.999 mole percent; wherein t is from about 0 to about 99.999 mole percent; and wherein a+j+t=100; GaQvWfSc (2) wherein G is as previously defined; wherein Q is as previously defined; wherein W is as previously defined, with the proviso that Q and W cannot both be the same; wherein S is selected from the group consisting of sulfomethylacrylamide and sulfoethylacrylamide; wherein a is from about 0.001 to about 10.00 mole percent; wherein v is from about 0 to about 97.999 mole percent; wherein f is from about 1 to about 97.999 mole percent; wherein c is from about 1 to about 40 mole percent; and wherein a+v+f+c=100.

As used herein, the term "GQW Polymer (Purple)" means a tagged treatment polymer as described in U.S. Pat. No. 7,601,789 (incorporated herein by reference) selected from the group consisting of: GaQjWt (1) wherein G is selected from the group consisting of:

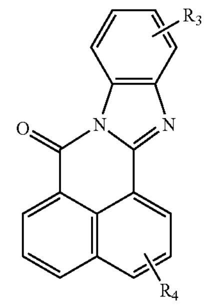

wherein R3 is sulfonic acid and its salts or carboxylic acid and its salts or allyloxy or vinylbenzyloxy; and R4 is sulfonic acid and its salts or carboxylic acid and its salts or allyloxy or 10 vinylbenzyloxy; with the proviso that when one of R3 or R4 is sulfonic acid and its salts or carboxylic acid and its salts, the other must be allyloxy or vinylbenzyloxy: wherein Q is selected from the group consisting of acrylic acid and salts thereof, methacrylic acid and salts thereof, maleic acid and salts thereof, maleic anhydride, acrylamide, crotonic acid, acrylamidomethylpropane sulfonic acid and salts thereof; wherein W is selected from the group consisting of: acrylic acid and salts thereof, methacrylic acid and salts thereof, itaconic acid and salts thereof, maleic acid and salts thereof, maleic anhydride, crotonic acid and salts thereof, acrylamide, methacrylamide, vinyl sulfonic acid, styrene sulfonate, N-tertbutylacrylamide, N-isopropylacrylamide, butoxymethylacrylamide, N,N-dimethylacrylamide, N,N-diethylacrylamide, dimethylaminoethyl acrylate methyl chloride quaternary salts, dimethylaminoethyl acrylate benzyl chloride quaternary salts, dimethylaminoethyl acrylate methyl sulfate quaternary salt, dimethylaminoethyl methacrylate methyl sulfate quaternary salt, dimethylaminoethyl acrylamide methyl sulfate quaternary salts, dimethylaminopropyl acrylamide methyl sulfate quaternary salts, dimethylaminopropyl methacrylamide methyl sulfate quaternary salts, diallyldimethyl ammonium chloride, N-vinyl formamide, dimethylamino ethyl methacrylate acid salts (including, but not limited to, sulfuric acid and hydrochloride acid salts), dimethylaminoethyl methacrylate methyl chloride quaternary salt, dimethylaminoethyl methacrylate benzyl chloride quaternary salt, methacrylamidopropyl trimethyl ammonium chloride, acrylamidopropyl trimethyl ammonium chloride, methylene bis acrylamide, triallylamine, acid salts of triallylamine, ethylene glycol dimethacrylate, hydroxymethylacrylate, hydroxyethylacrylate, hydroxypropylacrylate, hydroxypropylmethacrylate, diethylene glycol dimethacrylate, triethylene glycol dimethylacrylate, polyethylene glycol dimethacrylate, glycidyl methacrylate, acrylamidomethylpropane sulfonic acid and the sodium salt thereof, vinyl alcohol, vinyl acetate, and N-vinylpyrrolidone; with the proviso that Q and W cannot both be the same; wherein a is from about 0.001 to about 10.0 mole percent; wherein j is from about 0 to about 99.999 mole percent; wherein t is from about 0 to about 99.999 mole percent; and wherein a+j+t=100; GaQvWfSc (2) wherein G is as previously defined; wherein Q is as previously defined; wherein W is as previously defined, with the proviso that Q and W cannot both be the same; wherein S is selected from the group consisting of sulfomethylacrylamide and sulfoethylacrylamide; wherein a is from about 0.001 to about 10.00 mole percent; wherein v is from about 0 to about 97.999 mole percent; wherein f is from about 1 to about 97.999 mole percent; wherein c is from about 1 to about 40 mole percent; and wherein a+v+f+c=100.

Also, when a chromophore is used, any chromophore that interacts with (e.g., binds) aluminum (e.g., to form an alumino-chromophore hydroxide hydrate precipitate or particulate) to provide an emission response that varies based on oxoanion concentration can be used. The term "chromophore" generally refers to a molecule that absorbs certain wavelengths of visible light and reflects other wavelengths of visible light. In some examples, the chromophore includes one or more anionic pendant groups (e.g., 2, 3, 4 or more), which may be effective to interact and bind with an alumino-hydroxide-hydrate oligomer present in the aqueous solution undergoing evaluation. Example anionic pendant groups that can be used include carboxylate, sulfonate, sulfate, alcohol, and phosphate groups.

Independent of the specific fluorophore (or chromophore) or combinations of fluorophores (or chromophores) used (if any), the fluorophore (or chromophore) can be added to a static vessel containing the aqueous sample or a flowing stream of the aqueous sample. The fluorophore (or chromophore) may or may not be mixed (e.g., homogenously) with the aqueous sample to uniformly distribute the reagent throughout the aqueous solution. The amount of fluorophore (or chromophore) added to the sample can vary, e.g., based on the amount of sample undergoing analysis and emission response intensity of the fluorophore (or absorption properties of the chromophore). In some examples, the amount of fluorophore (or chromophore) added to the sample is less than 1 ppm by volume, such as less than 100 parts per billion (ppb) by volume, or less than 10 ppb by volume.

The technique of FIG. 1 also includes measuring the optical response of the optical analysis solution (16) and determining the concentration of the oxoanion in the aqueous solution based on the optical response (18). To measure the response of the optical analysis solution, one or more optical emitters associated with an optical sensor can direct light into the optical analysis solution and one or more optical detectors can be positioned to detect light from the optical analysis solution. In different examples, the light detected from the solution may be light transmitted through the solution or scattered by solids present in the solution (providing a transmittance and/or absorbance optical response, or colorimetric optical response in cases where an optically absorbing chromophore is present), light reflected by the solution (providing a turbidity optical response), and/or fluorescence light emanating from the solution in response to the emitted light (providing a fluorescence optical response). In any example, the optical response may vary depending on the concentration of oxoanion in the sample and, accordingly, the oxoanion concentration can be determined based on the optical response.

In instances where a fluorophore or chromophore is added to the optical analysis solution, the optical analysis solution may or may not be filtered prior to optically analyzing the optical analysis solution. Filtration can remove particulate from the optical analysis solution that can optically interfere with measurements of the fluorophore and/or chromophore not bound to the particulate. For example, as discussed above, a portion of the fluorophore or chromophore added to the optical analysis solution may become incorporated into Al Keggin ion-type structures (e.g., by binding to structures) formed by adding aluminum to the aqueous sample under evaluation. The amount of fluorophore or chromophore incorporated into the structures can vary depending on the oxoanion concentration in the aqueous solution, leaving free fluorophores or chromophores in the solution and bound fluorophores or chromophores. Filtration of particles containing bound fluorophore or chromophore can allow measurement of the free fluorophores or chromophores remaining in the solution while minimizing or eliminating interference from particulate or precipitation in the solution.

When performed, the optical analysis solution can be passed through any suitable size filter prior to being optically analyzed. In some examples, the optical analysis solution is passed through a filter having a pore size (e.g., average pore size, maximum pore size) of less than 10 microns, such as less than 5 microns, less than 1 micron, less than 0.5 microns, or less than 0.25 microns. In instances where progressively increasing amounts of aluminum-based reagent are added to the optical analysis solution, the optical analysis solution may be filtered after each portion of aluminum reagent is added and before the solution is optically analyzed.

In some examples, the optical analysis solution is optically analyzed by an optical sensor that directs light at one or more wavelengths into the optical analysis solution and thereafter detects light emanating from the solution. For example, the optical sensor may direct light into a stream or vessel of the optical analysis solution and detect the amount of light passing through the solution or scattered by solids present in the solution and generate therefrom an optical response of transmittance and/or absorbance. As another example, the optical sensor may direct light into a stream or vessel of the optical analysis solution and detect light scattered off the fluid (e.g., by particular or precipitate contained or suspended within the fluid), generating therefrom an optical response of turbidity. The light detected from the optical analysis solution when measuring absorption and/or turbidity may or may not be at the same frequency as the light emitted into the fluid to generate the optical response. For example, an optical emitter may emit light in the frequency range of approximately 220 nanometers (nm) to approximately 600 nm and an optical detector may detect light in a frequency range of approximately 300 nm to approximately 650 nm.

When a fluorophore is used, the optical sensor directs light into the optical analysis fluid and, in response to receiving the optical energy, fluorescing molecules within the fluid may excite, causing the molecules to produce fluorescent emissions. The fluorescent emissions, which may or may not be at a different frequency than the energy emitted by an optical emitter, may be generated as excited electrons within fluorescing molecules change energy states. The energy emitted by the fluorescing molecules may be detected by the optical detector. For example, an optical emitter may emit light in the frequency range of approximately 220 nm to approximately 600 nm and, depending on the composition of the fluid, cause fluorescent emissions in the range of approximately 300 nm to approximately 650 nm.

When a chromophore is used, the optical sensor can direct light into the optical analysis fluid at the characteristic wavelength(s) of the chromophore. The optical sensor can detect the amount of light passing through the solution at the characteristic wavelength(s) and generate therefrom a colorimetric optical response, for example measuring absorbance by the chromophore at the characteristic wavelength(s). The magnitude of absorbance can vary depending on the amount of chromophore in solution which, in turn, can vary based on the amount of chromophore incorporated into the Al Keggin ion-type structure.

The concentration of the oxoanion in the aqueous solution can be determined according to the technique of FIG. 1 based on the optical response of the optical analysis solution (18). The optical response data can be correlated with oxoanion concentration conversion information stored in memory (e.g., computer memory) to convert the optical response data into oxoanion concentration values. For example, when a predetermined (e.g., fixed) amount of aluminum-based reagent is added to the oxoanion-containing aqueous solution, the unknown oxoanion concentration in the solution can be determined with reference to calibration information stored in memory.

The calibration information can relate optical responses of multiple (e.g., 2, 3, 4, 5 or more) aqueous solutions having known concentrations of the same or similar oxoanions as those oxoanions expected to be present in the aqueous solution under evaluation having an unknown oxoanion concentration. Each of the different aqueous calibration solutions having known oxoanions concentrations can be prepared following the same or similar process as the process followed to prepare the aqueous solution under evaluation. For example, the same predetermined amount of aluminum-based reagent (e.g., providing the same aluminum concentration) can be added to each of the different aqueous calibration solutions and the calibration solutions can be optionally pH adjusted to the same or approximately same pH as the solution undergoing analysis. Further, each of the different aqueous calibration solutions can have a different known oxoanion concentration providing different optical responses across a range of different oxoanion concentrations (e.g., a range spanning an oxoanion concentration difference of at least 1000 ppm, such as at least 2000 ppm, at least 5000 ppm, or at least 10,000 ppm).

The calibration information may be stored, e.g., in a look-up table stored in memory that associates different optical response with different oxoanion concentration values. In another example, the data may be stored in the form of an equation that associates different optical response values with different oxoanion concentration values. Using the optical response value(s) generated from an aqueous solution having an unknown oxoanion concentration, a computer processor may determine the previously-unknown oxoanion concentration by referencing the stored look-up table, equation, or the like and determining (e.g., calculating, referencing) the oxoanion concentration corresponding to the optical response.

As another example, the optical response data can be correlated with oxoanion concentration conversion information stored in memory by using a molar ratio relating aluminum concentration at an optical inflection point to a known oxoanion concentration at that point. For example, when a progressively increasing amount of aluminum-based reagent is added to the oxoanion-containing aqueous solution, the unknown oxoanion concentration in the solution can be determined with reference to calibration information stored in memory relating aluminum concentration at an optical inflection point to oxoanion concentration.

The calibration information can be a molar ratio determined by generating optical responses of an aqueous solution having known concentrations of the same or similar oxoanions as those oxoanions expected to be present in the aqueous solution under evaluation having an unknown oxoanion concentration. The aqueous calibration solution having the known oxoanion concentrations can be prepared following the same or similar process as the process followed to prepare the aqueous solution under evaluation. For example, the same or similar progressively increasing amounts of aluminum-based reagent (e.g., providing the same aluminum concentration) can be added to the aqueous calibration solution and the calibration solution can be optionally pH adjusted to the same or approximately same pH as the solution undergoing analysis. The calibration solution can then be optically analyzed after each of the plurality of different portions of aluminum-based reagent are added to the solution. The amount of aluminum added to the solution when an optical inflection point is observed can then be correlated to the known oxoanion concentration in the calibration solution.

As one non-limiting example, progressively increasing amounts of aluminum-based reagent can be added to the aqueous solution in 10 ppm increments (based on the weight of the aluminum divided by the total weight of the solution). If the optical analysis solution exhibits an optical inflection point when a total of 120 ppm aluminum have been added to the solution, the known molar oxoanion concentration in the calibration solution can be divided by the molar aluminum concentration corresponding to 120 ppm aluminum to provide a molar ratio of moles of oxoanion/moles of aluminum, at the optical inflection point. This calibration information can be stored in memory (e.g., computer memory). Different molar ratios can be generated and stored for each of a plurality of different operation conditions (e.g., different pHs, different oxoanions).

In subsequent operation, a computer processor may identify the optical inflection point in a set of optical response values generated from an aqueous solution having an unknown oxoanion concentration. The optical inflection point can be a minimum optical response or maximum optical response (e.g., as measured in absorbance units, turbidity units, fluorescence emission intensity) when plotted versus increasing aluminum concentration. The computer processor can determine the amount of aluminum added to the aqueous solution that produced the optical response providing the optical inflection point. The computer processor can then determine the previously-unknown oxoanion concentration by referencing a molar conversion ratio (e.g., stored in a look-up table, equation, or the like) and determining (e.g., calculating, referencing) the oxoanion concentration corresponding to the aluminum concentration at the optical inflection location.

Figure 3:
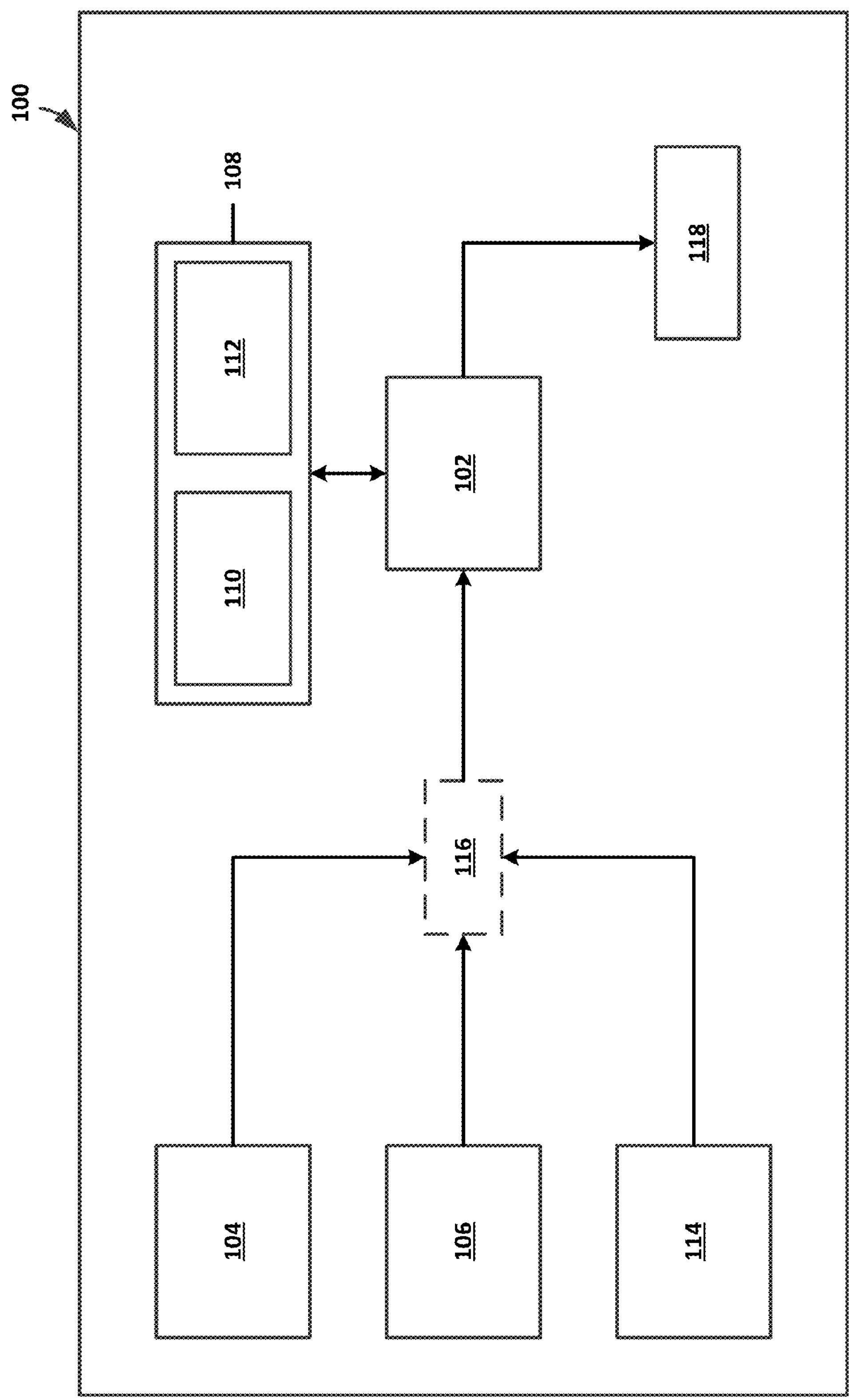
FIG. 3 is a conceptual diagram illustrating an example fluid system that can be used for on-site analysis of an aqueous solution to determine oxoanion concentration according to the example techniques of FIGS. 1 and 2.

FIG. 3 is a conceptual diagram illustrating an example fluid system 100, which may be used for on-site analysis of an aqueous solution to determine oxoanion concentration according to the example techniques of FIGS. 1 and 2 discussed above. In this example, the system 100 includes an optical sensor 102, an aqueous solution source 104 for supplying an aqueous solution comprising an unknown concentration of at least one oxoanion, and an aluminum reagent source 106. In general, the aqueous solution source 104 can be any source capable of providing an aqueous solution comprising at least one oxoanion. In some instances, the aqueous solution source 104 includes a tank of solution, seepage of solution, a process waste stream, or other source of solution. In some examples, the oxoanion-containing aqueous solution is sourced via a slip stream from a portion of a larger fluid volume. System 100 can be configured such that the aqueous solution source 104 and aluminum reagent source 106 are in fluid communication with the optical sensor.

System 100 in FIG. 3 also includes a controller 108 configured to measure and/or control system parameters and operation. Controller 108 includes memory 110 for storing data, including calibration information or other data used or acquired by system 100. Controller 108 also includes a processor 112 for controlling aspects of the system 100. For instance, processor 112 can be in communication with memory 110, or other controllable components of the system. For example, the system 100 can include one or more fluid control devices for controlling the flow of one or more fluids in the system 100, such as one or more pumps, valves, or other fluid flow controlling devices. The controller 108 can therefore direct the flow of an oxoanion-containing aqueous solution from the aqueous solution source 104 and an aluminum reagent from the aluminum reagent source 106 to the optical sensor 102. In some examples, the aqueous solution and the aluminum reagent can combine to form an optical analysis solution in the optical sensor 102. The system 100 can include a mixer 116 or other like device to receive and effectively combine the fluids to create the optical analysis solution prior to its entering the optical sensor 102. The system 100 can also include a filtration device (not illustrated in FIG. 3) to filter an optical analysis solution prior to optical analysis.

After leaving the optical sensor, the solution can be directed toward a drain 118 or, in some systems, back into the source of the aqueous solution downstream of the entry into the system 100. For example, a slip stream of aqueous solution from a larger process waste stream can be analyzed by the system 100 to determine the oxoanion concentration. After being analyzed in the optical sensor 102, the analyzed solution can be directed back into the process waste stream downstream from the aqueous solution source 104 from which the solution enters the system for analysis.

The optical sensor 102 can include one or more optical emitters configured to direct light into the optical analysis solution. The one or more optical emitters can include any appropriate emitter, such as lasers, light emitting diodes, and the like. In some examples, the one or more optical emitters are configured to emit light at one or more predetermined wavelengths. In further examples, the controller can control the wavelength(s) of light emitted from the one or more optical emitters into the optical analysis solution. The optical sensor 102 can also include one or more optical detectors configured to detect light from the optical analysis solution. The output from the one or more optical detectors can form an optical response that can be provided to controller 108 for storage and/or analysis.

In some examples, system 100 further includes an optional fluorophore or chromophore source 114. The fluorophore or chromophore source 114 can have associated therewith one or more pumps or valves controlled by the controller 108 for selectively dosing the fluorophore or chromophore to the mixer 116 and/or the optical sensor 102. The fluorophore can be such that it causes fluorescence of the optical analysis solution based on concentrations of various constituents and incent light. The chromophore can be such that it absorbs light at a characteristic wavelength, the magnitude of which varies based on concentrations of various constituents.

In various examples, the optical sensor 102 can be configured to detect one or more optical parameters of the optical analysis solution. For example, the optical sensor 102, in combination with the controller 108, can be configured to determine the turbidity or the absorbance of the optical analysis solution. In some embodiments, the optical sensor 102 can emit light toward the optical analysis solution and detect light that either scatters off or transmits through the solution in order to determine the turbidity or absorbance of the solution. The controller 108 can communicate with the optical sensor 102 to determine the turbidity or absorbance of the optical analysis solution.

In applications utilizing a fluorophore source 114, the optical sensor 102 can direct light toward the optical analysis solution to excite fluorescence of the optical analysis solution and detect the fluorescence emitted from the optical analysis solution. Accordingly, in such applications, the optical sensor 102 can include one or more optical emitters configured to emit light of varying wavelengths. For example, an optical sensor 102 can include an optical emitter configured to emit light at a first wavelength prone to scatter off of particulates suspended in the optical analysis solution, and can be used to measure the turbidity of the optical analysis solution. The optical sensor 102 can additionally or alternatively include an optical emitter configured to emit light at a second wavelength which excites fluorescence in the optical analysis solution, and can be used to measure the fluorescence thereof.

In some embodiments, the controller 108 is configured to control addition of the aluminum reagent (and/or fluorophore or chromophore) into the optical sensor 102 at a controlled rate. For example, the controller 108 can progressively increase the amount of aluminum reagent added to the system while observing the optical response via the optical sensor 102. In some examples, the controller 108 will progressively increase the amount of aluminum reagent in the aqueous solution until the observed optical response reaches an inflection point (e.g., a local minima or maxima). For example, in some instances, the optical response will increase as the aluminum reagent is added until an inflection point (e.g., the local maxima), after which the optical response will decrease with continued addition of the aluminum reagent. Conversely, in some instances, the optical response will decrease as the aluminum reagent is added until the inflection point is reached (e.g., the local minima), after which the optical response will increase with continued addition of the aluminum reagent. In some embodiments, the controller can determine the oxoanion concentration of the optical analysis solution based on the amount of aluminum reagent that corresponds to the inflection point. It should be noted that such occurrences are not mutually exclusive. For example, in some instances, the absorbance of the optical analysis solution reaches a local minima with the addition of the aluminum reagent, while the turbidity of the optical analysis solution reaches a local maxima with the addition of the aluminum reagent. It should also be noted that while the terms local minima and local maxima are used in portions of the disclosure, in some examples such terms can correspond to absolute minima and absolute maxima, respectively.

In some embodiments, the controller 108 is configured to dose a predetermined amount of aluminum reagent from the aluminum reagent source towards the optical sensor 102. In some such examples, the memory 110 can include calibration information corresponding to a calibrated relationship between a predetermined addition of aluminum reagent, an optical response, and the oxoanion concentration of an optical analysis solution. Accordingly, the calibration information can be used in conjunction with a measured optical response and determine the concentration of at least one oxoanion in the optical analysis solution at the predetermined amount of added aluminum reagent.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components.

The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following examples may provide additional details about oxoanion concentration determination techniques in accordance with this disclosure.

EXAMPLES

General Method

A series of solutions were prepared with known concentrations of various individual oxoanions: sulfate, molybdate, borate, chromate, and selenate. The solutions were each dosed with 50 ppb of PTSA (1,3,6,8-pyrenetetrasulfonic acid tetrasodium salt) and then dosed with small aliquots of polyaluminum chloride (Nalco Ultrion 8187). The solution pH was maintained at about 4.5 by addition of glacial acetic acid as needed. After 5-10 minutes of mixing, 3 ml of each solution was removed, filtered using a 0.45 micron filter, and optically analyzed by measuring fluorescence emission and/or turbidity. Each filtered sample was then returned to the original solution prior to the next Al dosage. The Al was generally dosed incrementally up to the highest oxoanion concentration supplied on a 1:1 ppm basis.

Example 1

Sulfate Response at Low Concentrations

Figure 4:
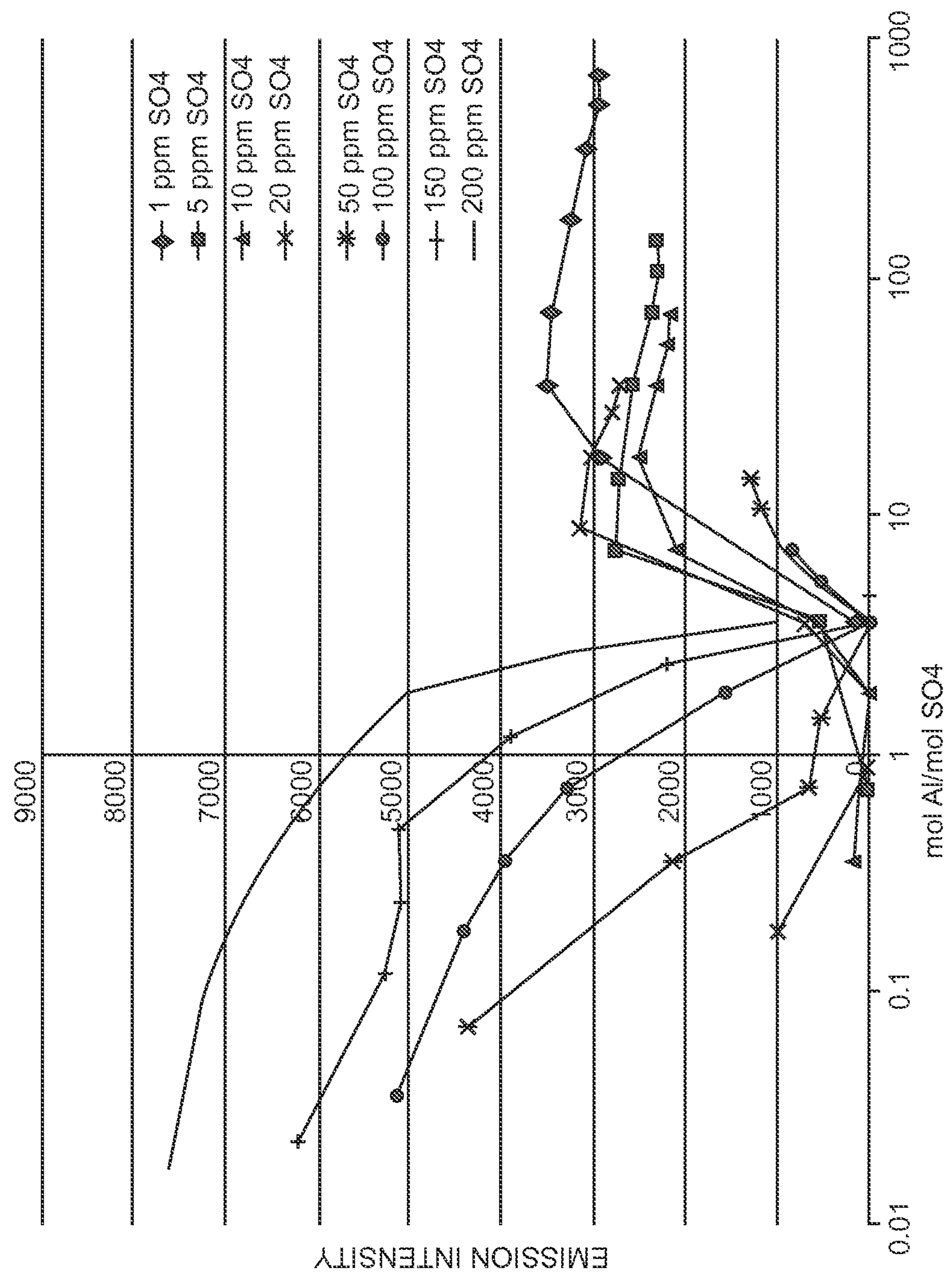
FIG. 4 is a plot showing example experimental fluorescent emission response data as a function of Al dose and sulfate concentration.

In this case, seven 200 ml sulfate solutions were prepared from a sodium sulfate solution. The concentrations tested were 1, 5, 10, 20, 50, 100, 150, and 200 ppm. As mentioned above, the Al was increased incrementally in each solution and the resulting PTSA emission and turbidity measured. FIG. 4 demonstrates the PTSA emission response as a function of the Al:$SO_4$ ratio. As the Al concentration increased, the emission of the fluorophore decreased to near zero at an Al:$SO_4$ ratio ranging from approximately 2 to approximately 5, then increased above that ratio. Difficulty feeding very low dosages of the Al reagent and the small amount of aluminum complex formed in the low sulfate solutions likely prevented observation of a response. Adjusting the PTSA concentration and utilizing a more accurate aluminum reagent dosing system likely would allow observation of a lower sulfate response.

Figure 5:
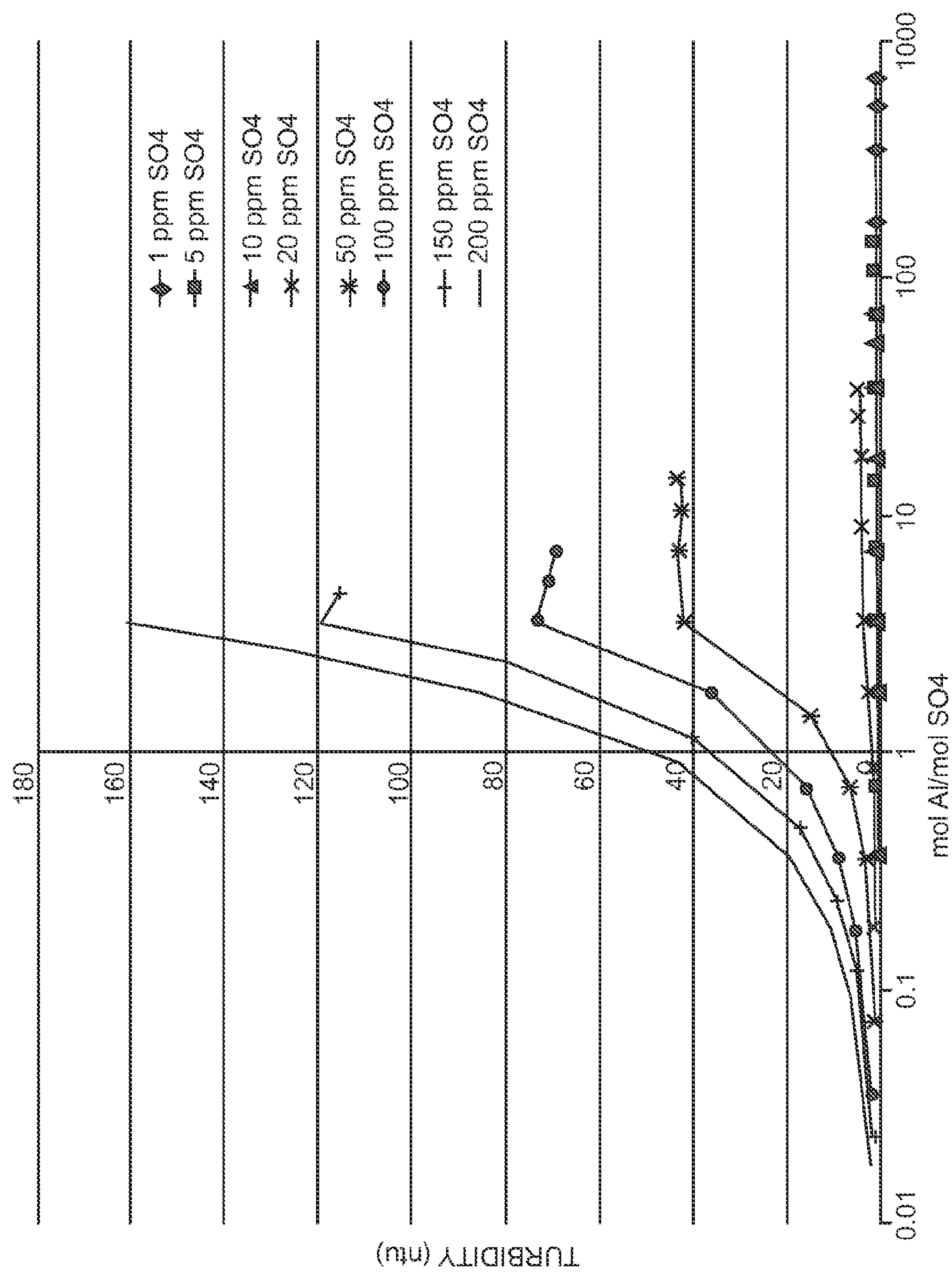
FIG. 5 is a plot showing example experimental turbidity response data as a function of sulfate concentration and Al dosage.

A consistent trend was observed in the turbidity as well (FIG. 5). No change was detected in the turbidity at low sulfate concentrations (e.g., 1, 5, and 10 ppm sulfate) under the conditions tested. However, once the sulfate concentration was at least 50 ppm, the turbidity began to increase with increasing Al concentration. The turbidity either plateaued or decreased once a mole ratio ranging from approximately 3 to approximately 4 was reached.

Example 2

Sulfate Response at High Concentrations

Figure 6:
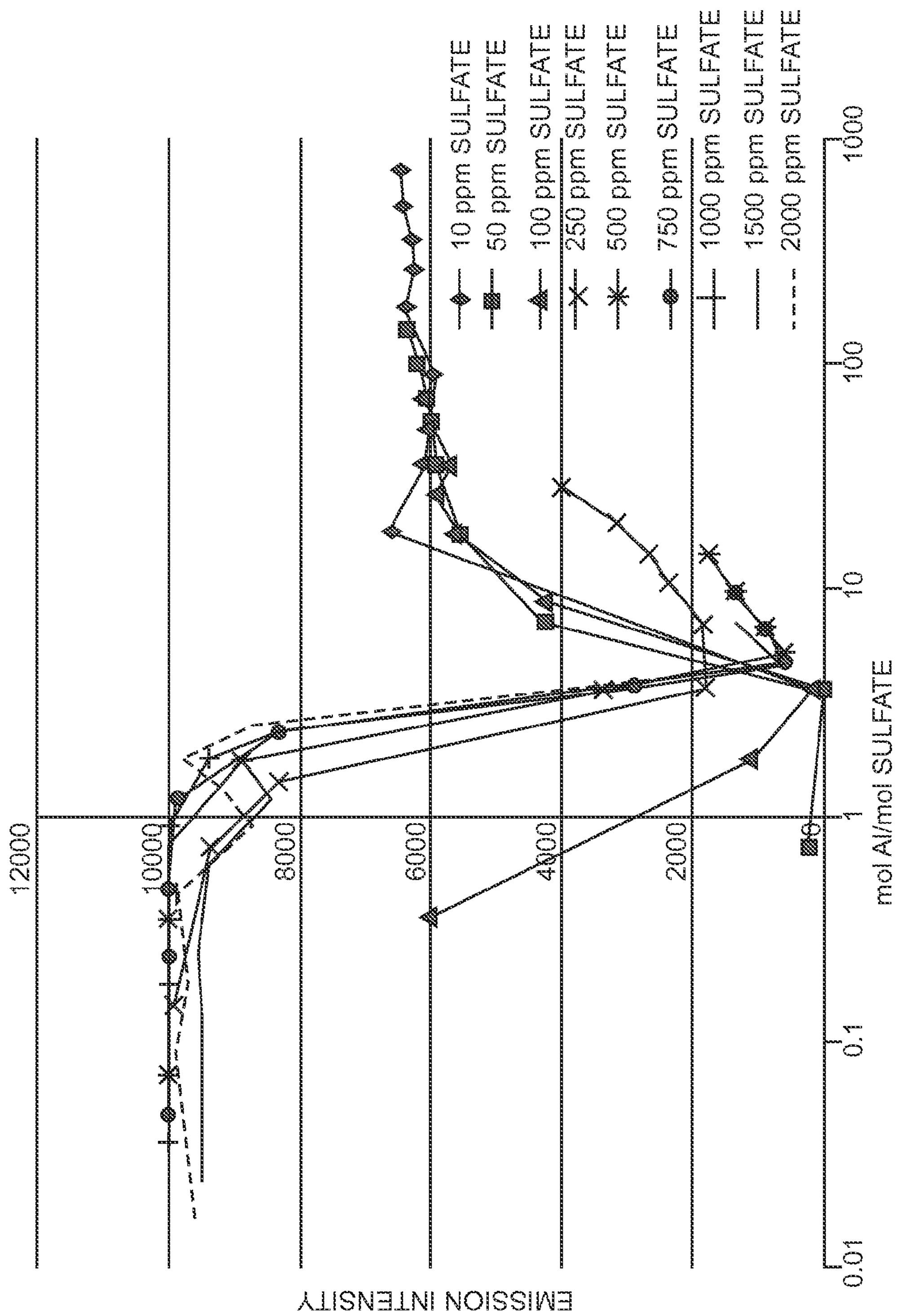
FIG. 6 is a plot showing additional example experimental fluorescent emission response data as a function of Al dose and sulfate concentration.

A series of 100 ml solutions were prepared with different sulfate concentrations using a 10,000 ppm stock sulfate solution. The solutions were dosed with the aluminum reagent with the Al dosage increased incrementally in each solution. The emission and turbidity resulting after each aluminum dose increment was measured as described above. As the sulfate concentration increased, more Al was needed to minimize the fluorescence and maximize the turbidity before inflection. The general trend was similar to sulfate at low concentrations. The Al concentration used to produce the fluorescence emission minima for each sulfate concentration is shown in FIG. 6. The relationship between the Al and sulfate concentrations was linear in the range from 10 ppm sulfate up to 1500 ppm sulfate.

Figure 7:
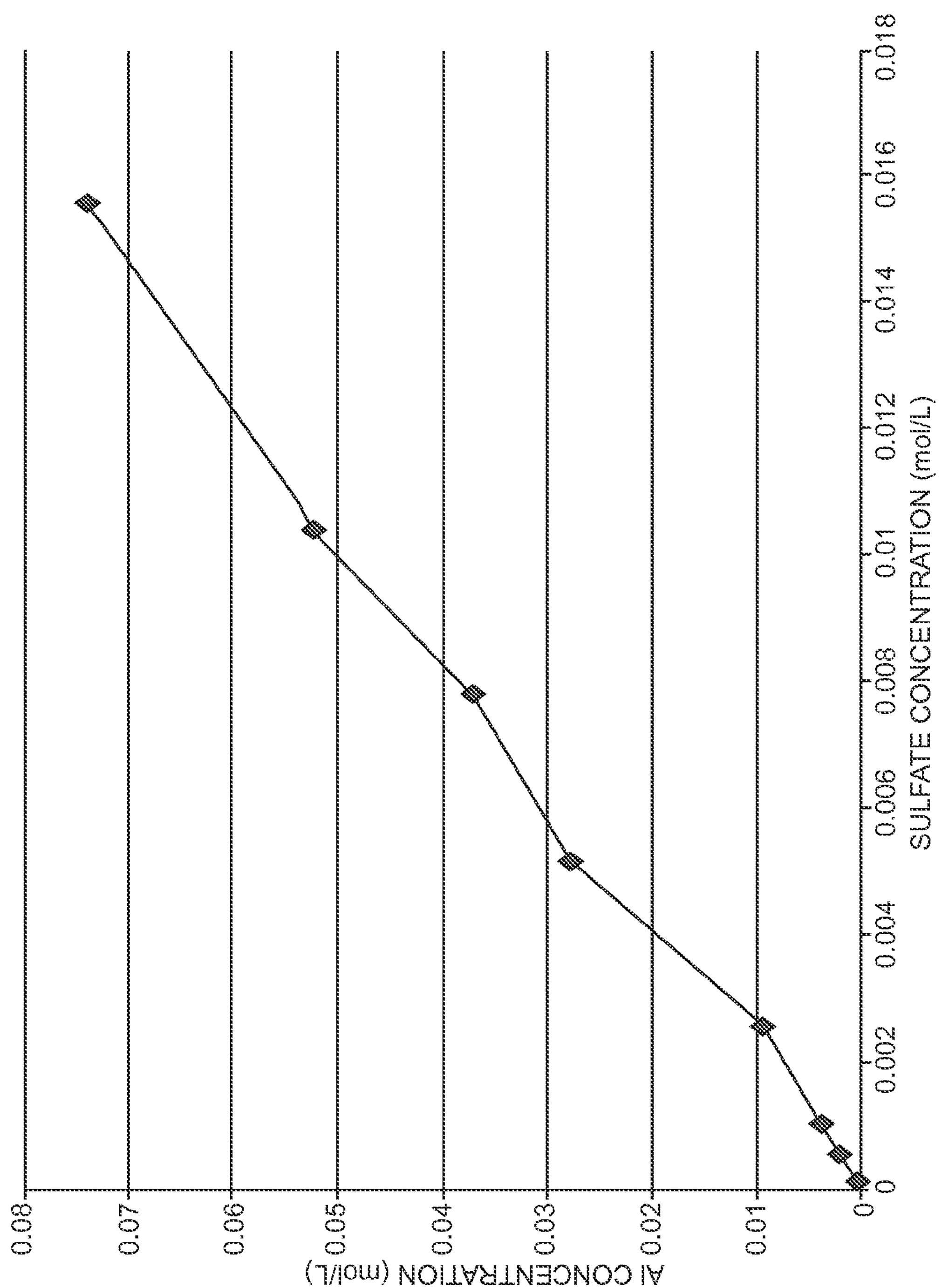
FIG. 7 is a plot showing example Al concentrations at the fluorescent emission minima for different example sulfate solutions.
Figure 8:
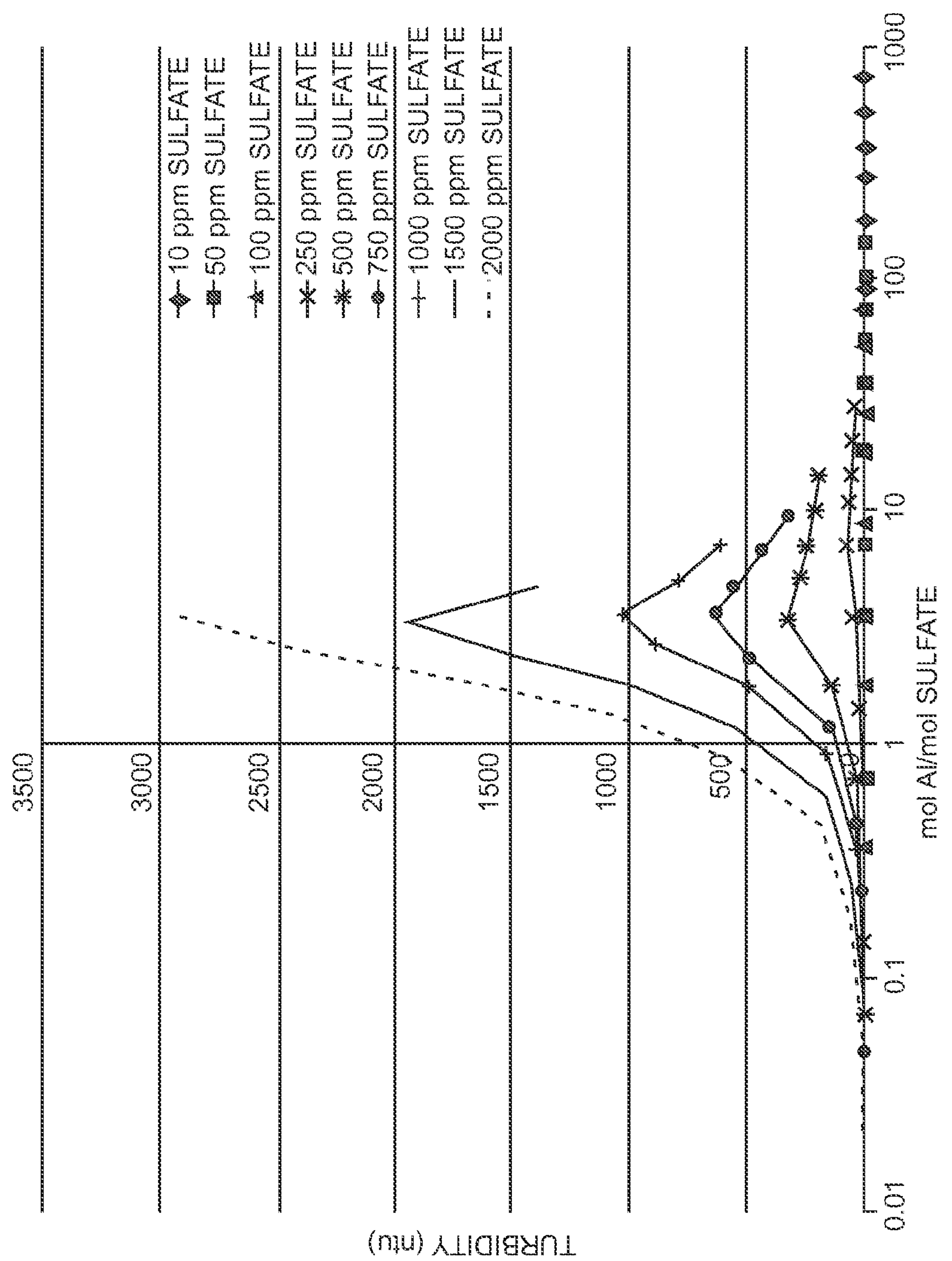
FIG. 8 is a plot showing additional example experimental turbidity response data as a function of sulfate concentration and Al dosage.

FIG. 7 shows the aluminum concentration at the emission minima for each sulfate solution tested. Further, similar to Example 1, the turbidity for each sulfate solution exhibited a maximum at a particular Al:$SO_4$ molar ratio (approximately 3.5). This is shown in FIG. 8.

Example 3

Molybdate Response

Figure 9:
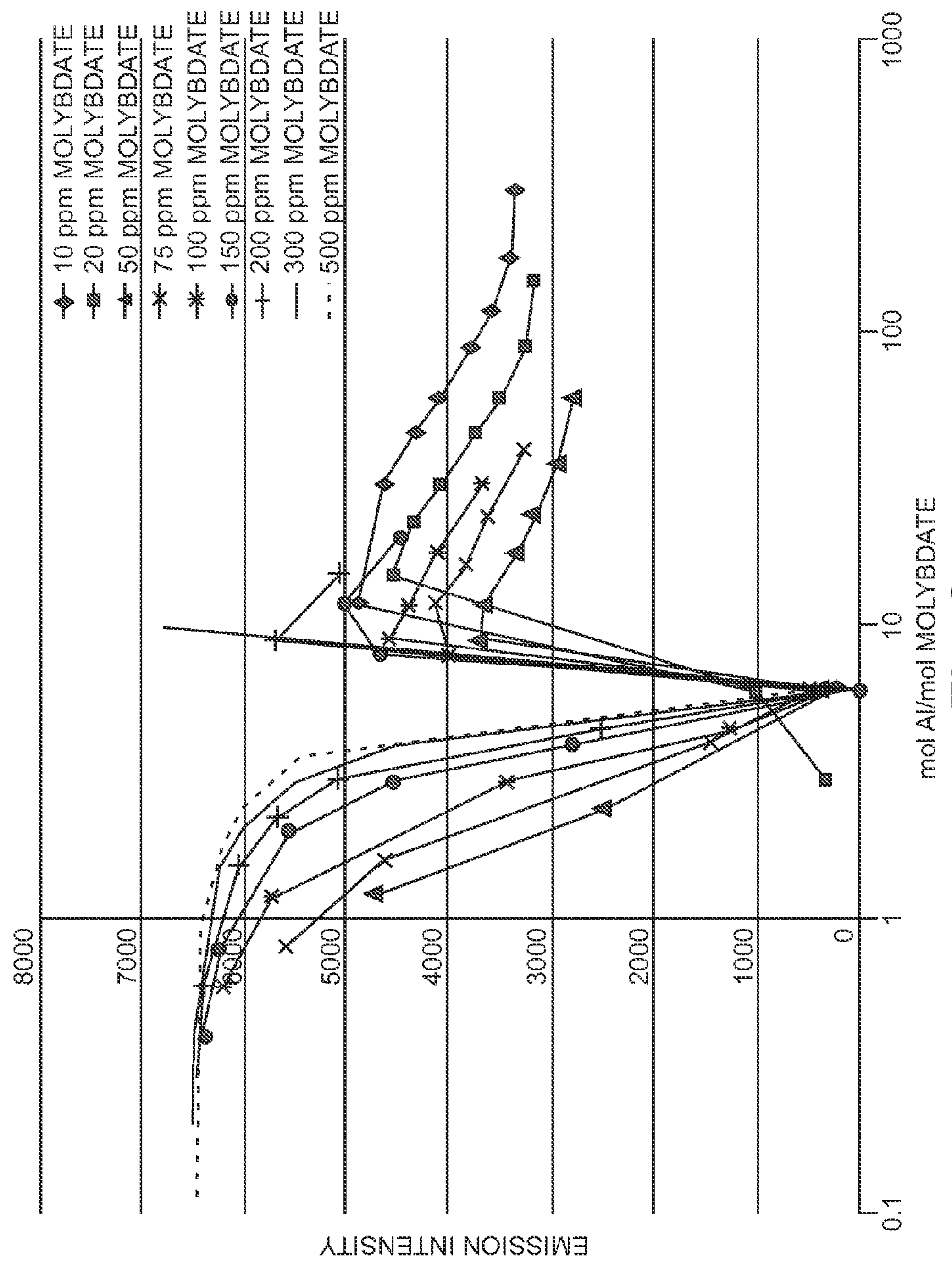
FIG. 9 is a plot showing example experimental fluorescent emission response data as a function of Al dose and molybdate concentration.
Figure 10:
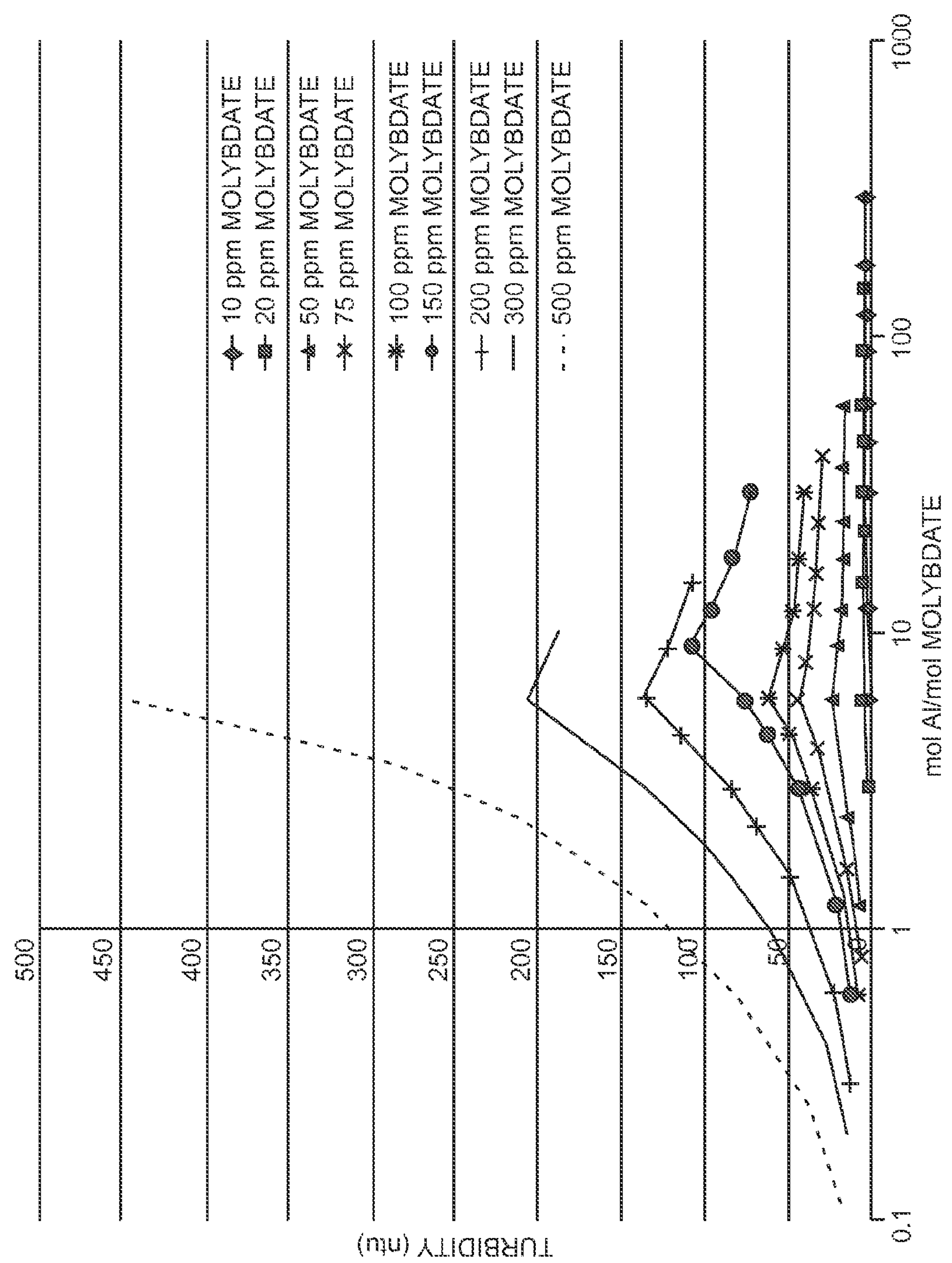
FIG. 10 is a plot showing example experimental turbidity response data as a function of molybdate concentration and Al dosage.

Similar behavior to that exhibited when testing sulfate was observed in a series of molybdate solutions with varying concentrations: 10, 20, 50, 75, 100, 150, 200, 300, and 500 ppm molybdate. The Al dosage was incrementally added to match the ppm values of the molybdate at a 1:1 ratio. Above the 20 ppm level, all of the emission minima occurred at a Al:$MoO_4$ ratio of approximately 6 (FIG. 9). The effect of Al dosage on the turbidity response was similar (FIG. 10). At an Al:$MoO_4$ mole ratio of approximately 6, the turbidity began to increase with molybdate concentrations of approximately 50 ppm or more.

Example 4

Chromate Response

Figure 11:
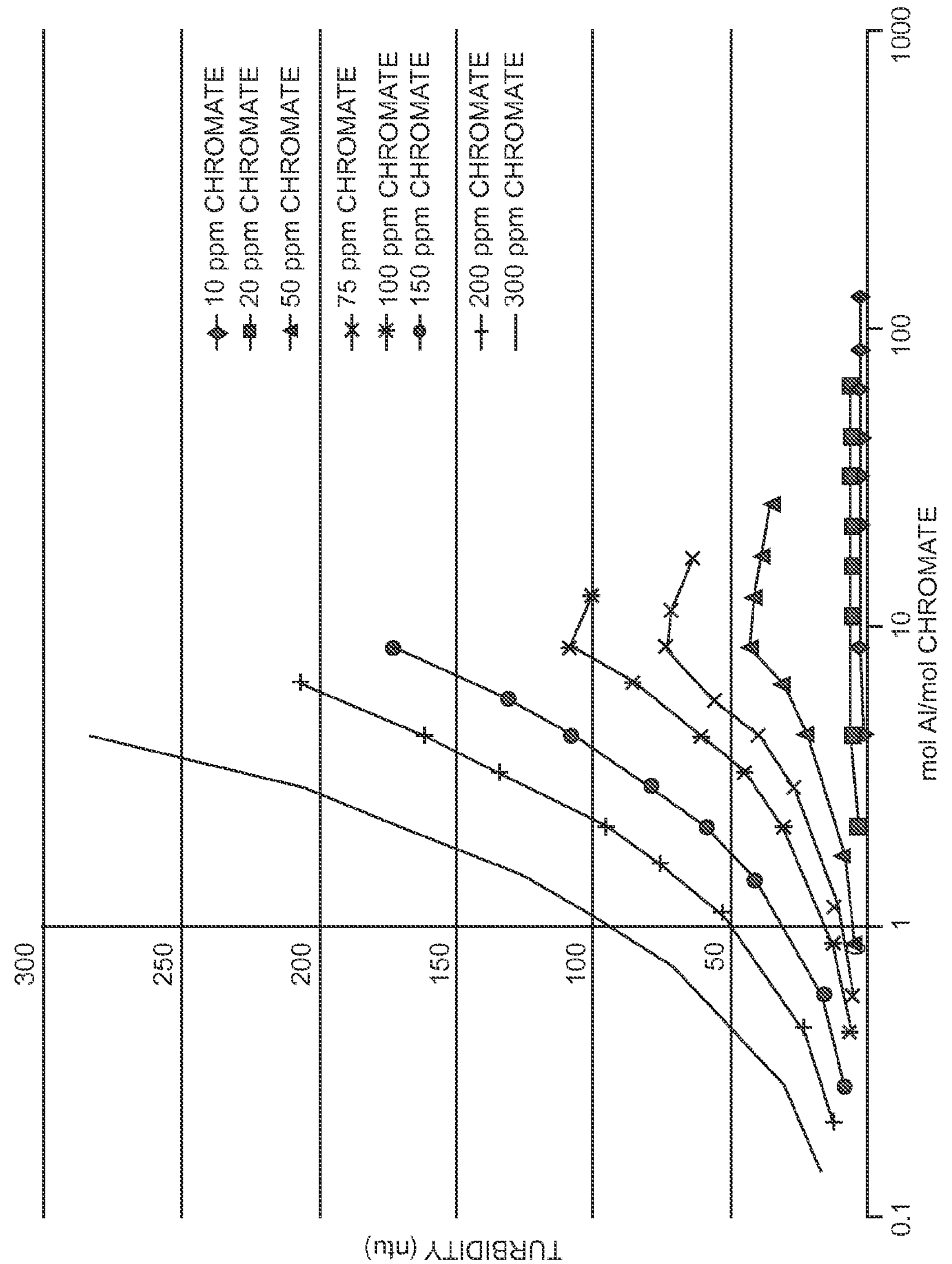
FIG. 11 is a plot showing example experimental turbidity response data as a function of chromate concentration and Al dosage.

Similar experiments to those performed on sulfate were conducted with a series of chromate solutions at different concentrations. Due to the emissivity profile of chromate in response to UV excitation in the range of the fluorophore, the fluorescence response was not tested. However, the turbidity of the solutions demonstrated a response as a function of Al dosage. The turbidity began increasing until an Al/Chromate molar ratio of approximately 8.6 was reached, at which point the turbidity began to decrease (FIG. 11).

Example 5

Selenate Response

Figure 12:
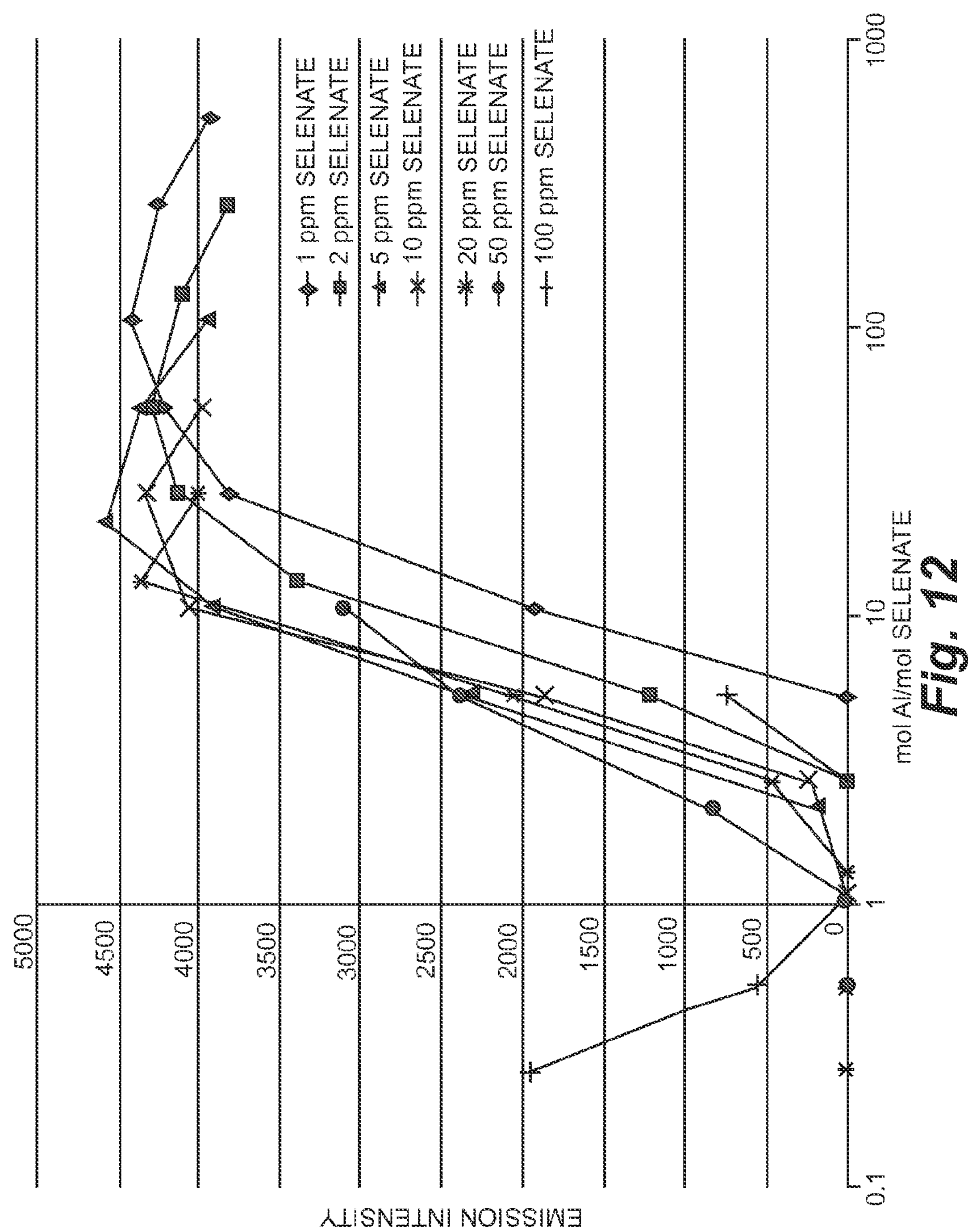
FIG. 12 is a plot showing example experimental fluorescent response data as a function of selenate concentration and Al dosage.

In contrast to the chromate solutions, selenate solutions did not exhibit any turbidity response as a function of Al dosage. However, a fluorescence response was observed where the emission intensity began at zero (for most $SeO_4$ concentrations) and then increased with increasing Al concentrations (FIG. 12).

Example 6

Borate Response

Figure 13:
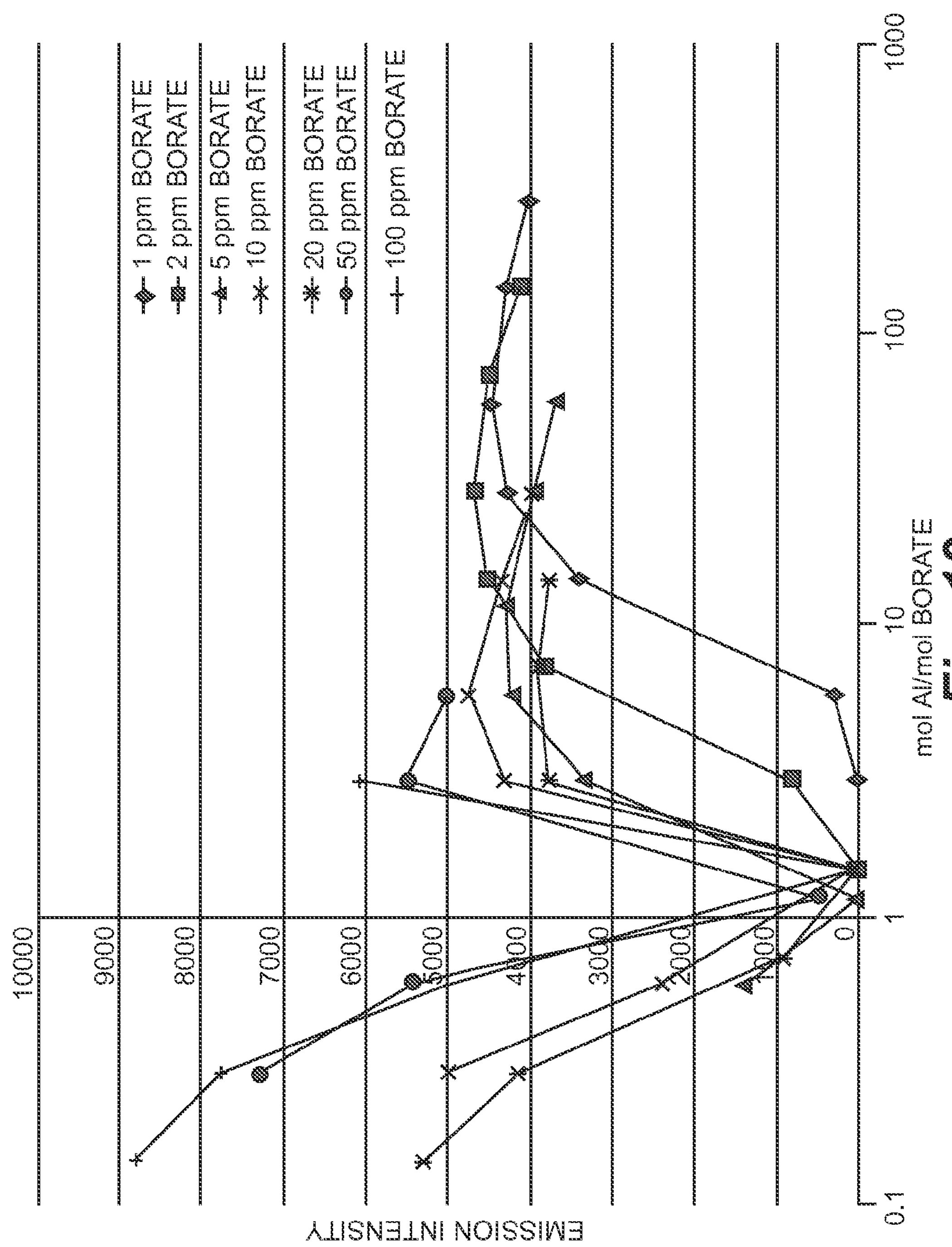
FIG. 13 is a plot showing example experimental fluorescent response data as a function of borate concentration and Al dosage.

A similar response to selenate was observed when using borate as the oxoanion. The borate solutions did not exhibit any turbidity, limiting the response to the drop in fluorescence emission intensity at a molar ratio ranging from approximately 1 to approximately 2 (FIG. 13). Similar to the selenate, both the 1 and 2 ppm borate solution emission responses were broader than at higher concentrations.

Example 7

Arsenate Response

Figure 14:
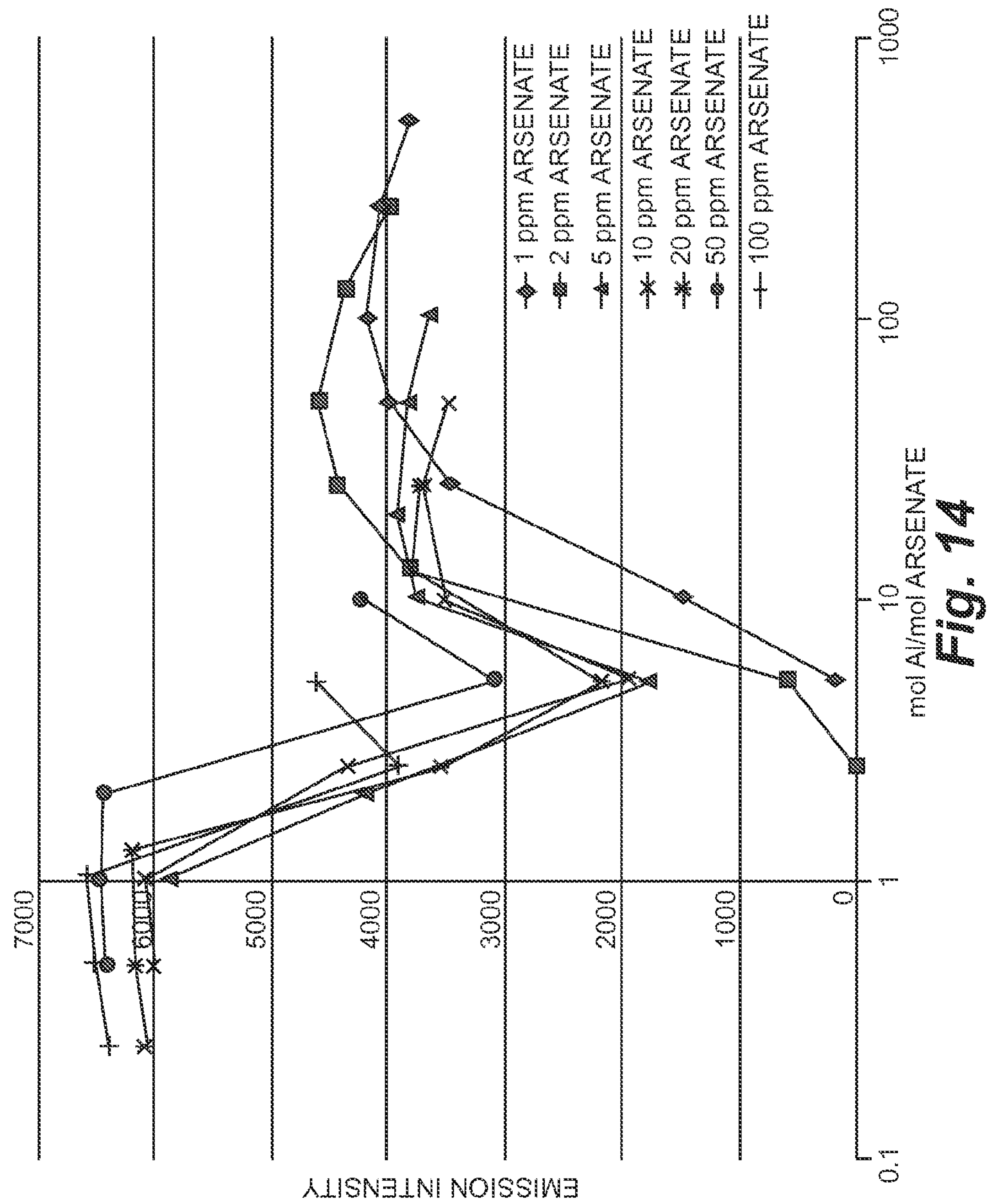
FIG. 14 is a plot showing example experimental fluorescent response data as a function of arsenate concentration and Al dosage.

Arsenate solutions at identical concentrations were also evaluated for a fluorescence response as the solutions did not exhibit any turbidity when dosed with Al. The emission intensity demonstrated a minimum at a molar ratio ranging from approximately 2 to approximately 5 (FIG. 14). Both 1 and 2 ppm arsenate solutions exhibited similar Al dose responses at the same concentrations as the selenate and borate solutions.

Example 8

Comparison of Oxoanions Responses

Figure 15:
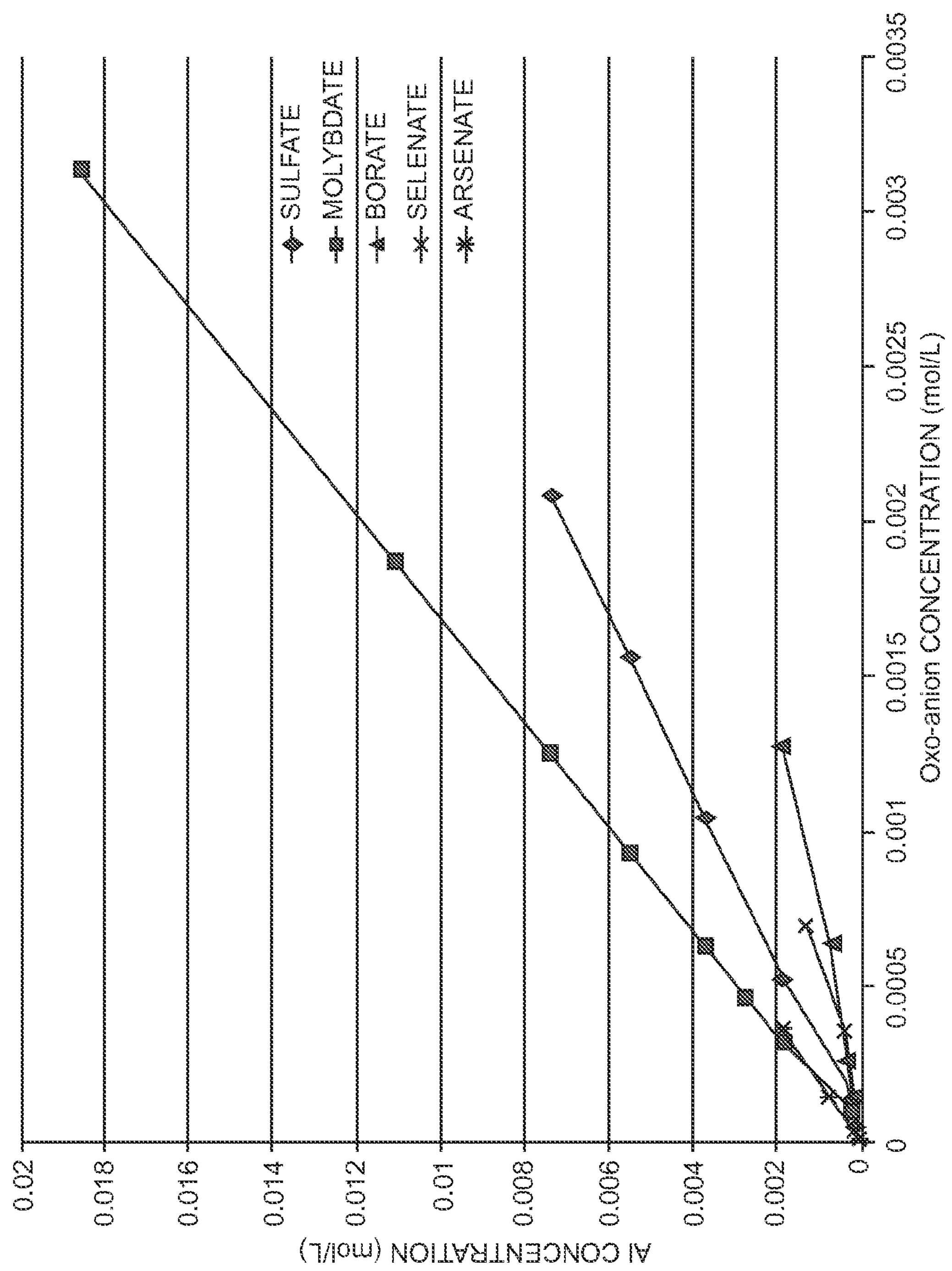
FIG. 15 is a plot showing example linear relationships between oxoanion concentrations and Al concentrations at fluorescent emission minima.
Figure 16:
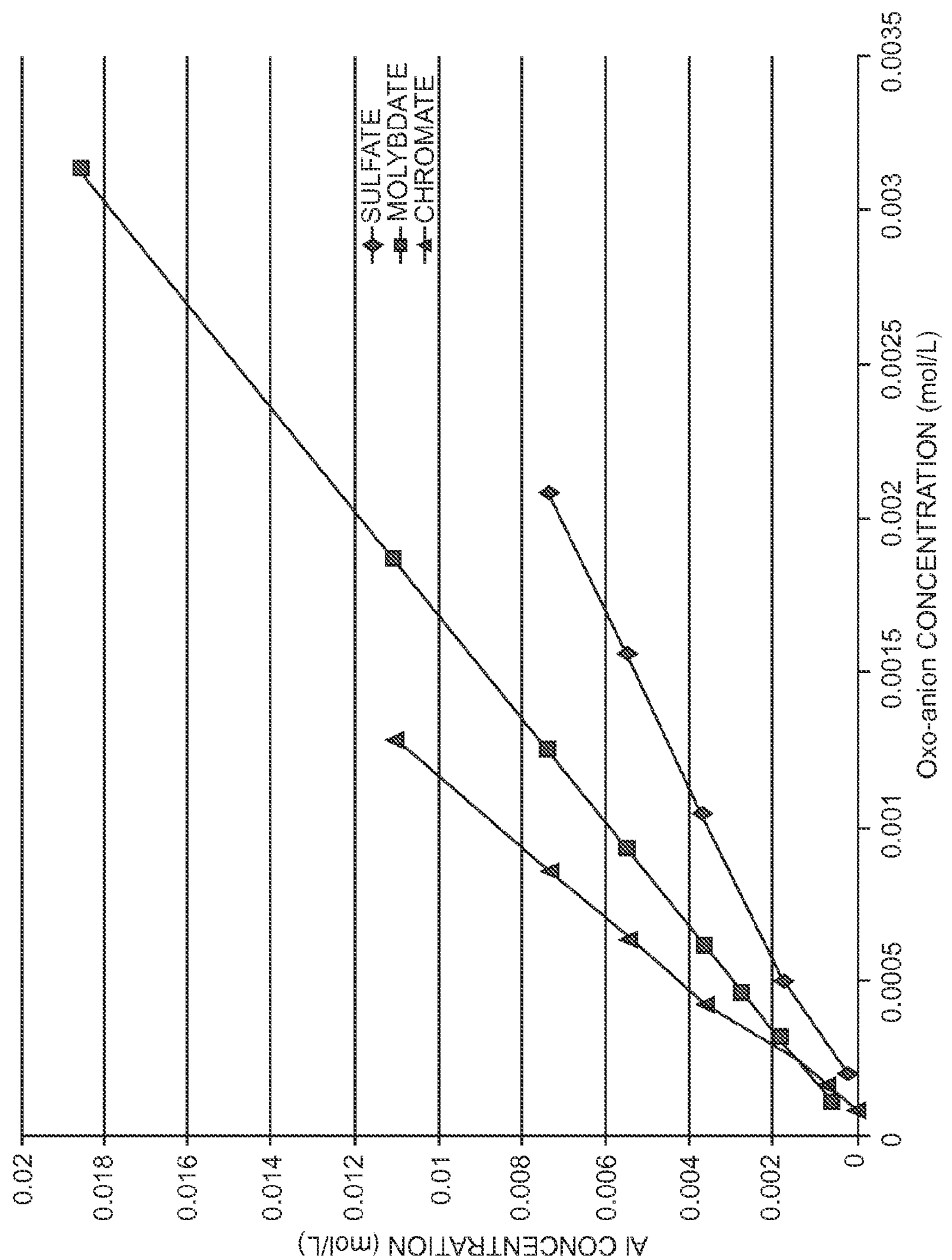
FIG. 16 is a plot showing example linear relationships between oxoanion concentrations and Al concentrations at turbidity maxima.

As described in the previous examples, similar experiments to sulfate were conducted with other oxoanions such as molybdate, chromate, selenate, and borate. For these examples described above, only sulfate and molybdate could be measured via both fluorescence and turbidity with the experimental apparatus used and under the experimental conditions tested. Only the turbidity of the chromate solutions in response to the Al dosage was measured due to spectroscopic interferences. Neither the selenate nor the borate exhibited any detectable turbidity during the experiment under the conditions tested. Each of the oxoanions demonstrated similar behavior to the sulfate data shown above. The linear relationship between the oxoanion concentration (sulfate from Example 1, molybdate from Example 3, selenate from Example 5, borate from Example 6, and arsenate from Example 7) and the Al concentration at the fluorescence emission minima is shown in FIG. 15. A similar linear relationship between the oxoanion concentration (sulfate from Example 1, molybdate from Example 3, and chromate from Example 4) and the Al concentration at the turbidity maxima is shown in FIG. 16.

Example 9

Response of PTSA

Figure 17:
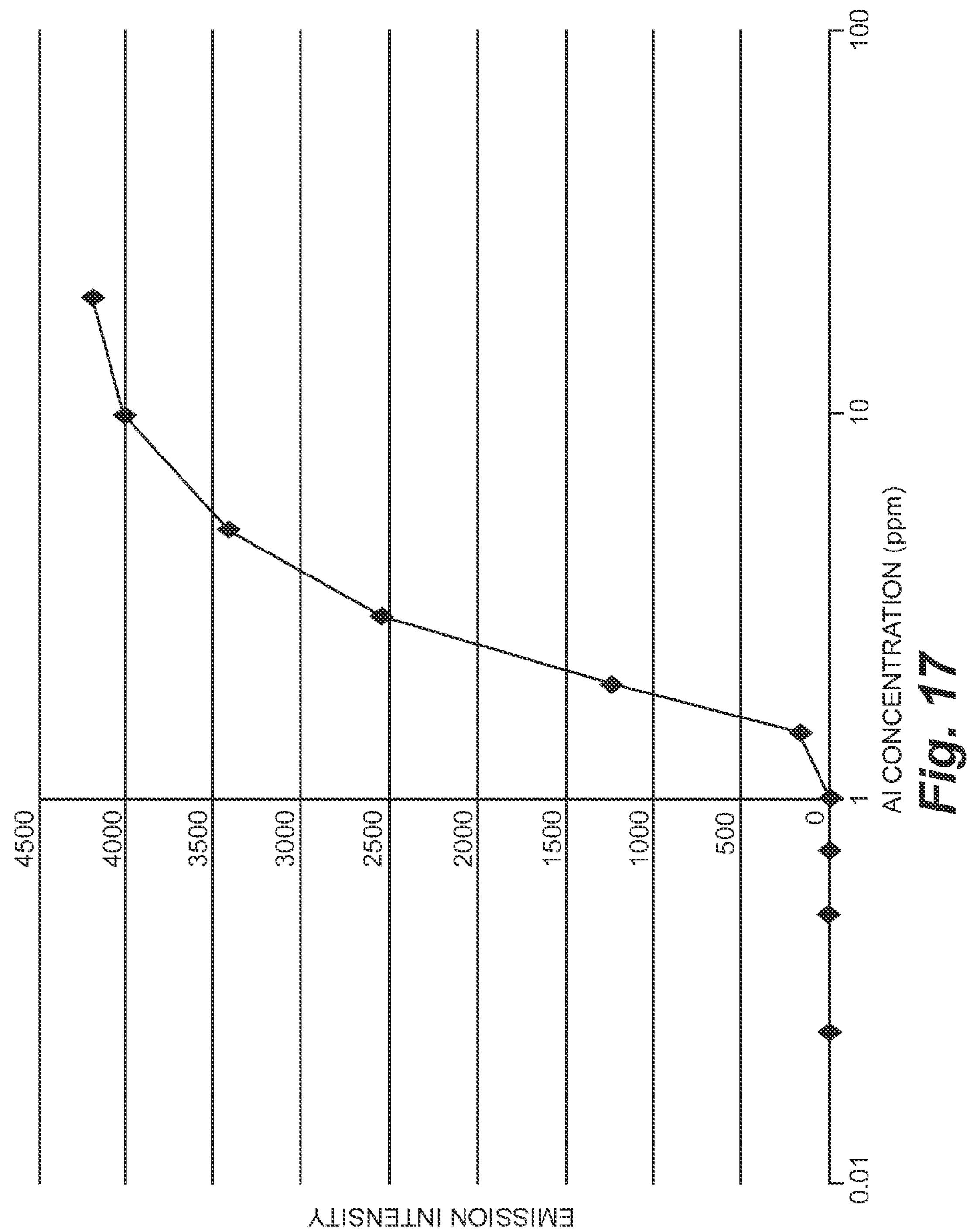
FIG. 17 is a plot showing example fluorescent emission response of an example fluorophore in the absence of any oxoanaions as a function of Al concentration.

A control experiment was performed testing the optical response of the fluorophore PTSA when dosed with Al in the absence of oxoanions. In the experiment, 2 L of 50 ppb PTSA solution was treated incrementally with Al from 0.25 ppm up to 20 ppm. As shown in FIG. 14, the intensity remained at 0 until the Al concentration was more than 1 ppm. At an Al concentration of approximately 10 ppm, the emission intensity appeared to plateau. The solution did not exhibit any change in the turbidity. FIG. 17 illustrates the fluorescence emission response of 50 ppb PTSA as a function of Al concentration.

The invention claimed is:

1. A method comprising:

adding an aluminum reagent to an aqueous solution having an unknown concentration of an oxoanion and thereby forming an optical analysis solution;

directing light into the optical analysis solution and determining therefrom an optical response of the optical analysis solution; and determining a concentration of the oxoanion in the aqueous solution having the unknown concentration of the oxoanion based on the optical response of the optical analysis solution.

2. The method of claim 1, wherein the optical response comprises at least one of light scattering, transmittance, and absorbance.

3. The method of claim 1, wherein adding the aluminum reagent to the aqueous solution having the unknown concentration of the oxoanion comprises adding a progressively increasing amount of the aluminum reagent to the aqueous solution until the optical response of the optical analysis solution exhibits an inflection point, and determining the concentration of the oxoanion in the aqueous solution having the unknown concentration of the oxoanion comprises determining the concentration of the oxoanion based on the amount of aluminum reagent corresponding to the inflection point of the optical response of the optical analysis solution.

4. The method of claim 3, wherein the inflection point is one of a minima and a maxima, and wherein, when the inflection point is a minima, the optical response is absorbance or fluorescence, and when the inflection point is a maxima, the optical response is light scattering or transmittance.

5. The method of claim 3, wherein determining the concentration of the oxoanion based on the amount of aluminum reagent corresponding to the inflection point of the optical response comprises calculating the concentration of the oxoanion using a molar ratio ranging from one mole of oxoanion per three moles of aluminum to one mole of oxoanion per six moles of aluminum.

6. The method of claim 5, wherein the molar ratio ranges from approximately 3.7 to approximately 4.9.

7. The method of claim 1, wherein adding the aluminum reagent to the aqueous solution having the unknown concentration of the oxoanion comprises adding a predetermined amount of the aluminum reagent to the aqueous solution, and determining the concentration of the oxoanion in the aqueous solution having the unknown concentration of the oxoanion comprises determining the concentration of the oxoanion based on calibration information relating optical responses to oxoanion concentrations at the predetermined amount of aluminum reagent.

8. The method of claim 1, further comprising adjusting a pH of the aqueous solution to a pH below 8.

9. The method of claim 8, wherein adjusting the pH of the aqueous solution comprises adding an acid to adjust the pH to a range from approximately 3 to approximately 6.

10. The method of claim 1, wherein the oxoanion has the formula $A_xO_y^{z-}$, where A is a chemical element selected from the group consisting of Se, P, As, Cr, B, Mo, V, and S; X is an integer having a value of 1 or 2; O is oxygen; Y is an integer having a value of at least 1; and Z is an integer having a value of at least 2.

11. The method of claim 1, wherein the oxoanion is sulfate.

12. The method of claim 1, wherein the aluminum reagent comprises at least one of sodium aluminate, calcium aluminate, aluminum chloride, polyaluminum chloride, aluminum hydroxide, aluminum acetate, and aluminum nitrate.

13. The method of claim 1, further comprising adding a fluorophore to the aqueous solution, and wherein the optical response comprises fluorescence.

14. The method of claim 13, wherein the fluorophore comprises one or more anionic pendant groups.

15. The method of claim 14, wherein the one or more anionic pendant groups comprise sulfonic acid and salts thereof.

16. The method of claim 13, wherein the fluorophore comprises at least one of 1,3,6,8-pyrenetetrasulfonic acid, 1-pyrenesulfonic acid, 8-hydroxy-1,3,6-pyrenetrisulfonic acid, y-oxo-1-pyrenebutyric acid, 1-pyrenecarboxylic acid, 1,5-naphthalenedisulfonic acid, 4-chloro-2-phenyleiminomethylphenol, N,N'-disalicylidene-1,3-diamino-2-hydroxypropane, and 1-naphthalene sulfonic acid.

17. The method of claim 13, further comprising adjusting the pH of the aqueous solution to a range from approximately 3 to approximately 6, and wherein the oxoanion has the formula $A_xO_y^{z-}$, where A is a chemical element selected from the group consisting of Se, P, As, Cr, B, Mo, V, and S; X is an integer having a value of 1 or 2; O is oxygen; Y is an integer having a value of at least 1; and Z is an integer having a value of at least 2.

18. The method of claim 13, wherein the fluorophore comprises 1,3,6,8-pyrenetetrasulfonic acid and the oxoanion comprises sulfate.

19. The method of claim 13, further comprising filtering the optical analysis solution prior to directing light into the optical analysis solution and determining therefrom the optical response of the optical analysis solution.

20. The method of claim 1, further comprising adding a chromophore to the aqueous solution, and wherein the optical response comprises absorbance at a characteristic wavelength of the chromophore.

21. The method of claim 1, further comprising drawing a slip stream of the aqueous solution having the unknown concentration of the oxoanion, adjusting a pH of the slip stream, adding a fluorophore, and determining the concentration of the oxoanion based on the fluorometric optical response of the optical analysis solution.

22. The method of claim 1, further comprising controlling a process at least one of generating, treating, or processing the aqueous solution having the unknown concentration of oxoanion based on the determined concentration of the oxoanion.

23. A system comprising:

a source of an aqueous solution having an unknown concentration of an oxoanion;

an aluminum reagent source configured to supply aluminum reagent to the aqueous solution and thereby form an optical analysis solution;

an optical sensor that comprises an emitter configured to direct light into the optical analysis solution; and a detector configured to detect light from the optical analysis solution and provide therefrom an optical response; and a controller configured to determine a concentration of the oxoanion in the aqueous solution having the unknown concentration of the oxoanion based on the optical response of the optical analysis solution.

24. The system of claim 23, wherein the optical response is one of light scattering, transmittance, and absorbance.

25. The system of claim 23, wherein the controller is further configured to control addition of the aluminum reagent to the aqueous solution having the unknown concentration of the oxoanion comprises by adding a progressively increasing amount of the aluminum reagent to the aqueous solution until the optical response of the optical analysis solution exhibits an inflection point, and the controller is configured to determine the concentration of the oxoanion in the aqueous solution having the unknown concentration of the oxoanion by at least determining the concentration of the oxoanion based on the amount of aluminum reagent corresponding to the inflection point of the optical response of the optical analysis solution.

26. The system of claim 25, wherein the controller is configured to determine the concentration of the oxoanion based on the amount of aluminum reagent corresponding to the inflection point of the optical response by at least calculating the concentration of the oxoanion using a molar ratio ranging from one mole of oxoanion per three moles of aluminum to one mole of oxoanion per six moles of aluminum.

27. The system of claim 26, wherein the molar ratio ranges from approximately 3.7 to approximately 4.9.

28. The system of claim 23, wherein the controller is further configured to control addition of the aluminum reagent to the aqueous solution having the unknown concentration of the oxoanion comprises by adding a predetermined amount of the aluminum reagent to the aqueous solution, and the controller is configured to determine the concentration of the oxoanion in the aqueous solution having the unknown concentration of the oxoanion by at least determining the concentration of the oxoanion based on calibration information relating optical responses to oxoanion concentrations at the predetermined amount of aluminum reagent.

29. The system of claim 23, further comprising a source of an acid, wherein the controller is configured to adjust the pH of the aqueous solution to a range from approximately 3 to approximately 6 by at least controlling addition of the acid to the aqueous solution.

30. The system of claim 23, further comprising a source of at least one of a fluorophore and a chromophore, wherein the controller is configured to control addition of the fluorophore or chromophore to the aqueous solution, and wherein the optical response comprises one of fluorescence and absorbance at a characteristic wavelength of the chromophore.

31. The system of claim 30, wherein the fluorophore comprises one or more anionic pendant groups comprising sulfonic acid and salts thereof.

32. The system of claim 30, further comprising a source of an acid, wherein the controller is configured to adjust the pH of the aqueous solution to a range from approximately 3 to approximately 6 by at least controlling addition of the acid to the aqueous solution, and wherein the oxoanion has the formula $A_xO_y^{z-}$, where A is a chemical element selected from the group consisting of Se, P, As, Cr, B, Mo, V, and S; X is an integer having a value of 1 or 2; O is oxygen; Y is an integer having a value of at least 1; and Z is an integer having a value of 2.

33. The system of claim 23, wherein the oxoanion is sulfate and the aluminum reagent comprises at least one of sodium aluminate, calcium aluminate, aluminum chloride, polyaluminum chloride, aluminum hydroxide, aluminum acetate, and aluminum nitrate.

* * * * *